US009416383B2

(12) United States Patent
Thakker et al.

(10) Patent No.: US 9,416,383 B2
(45) Date of Patent: Aug. 16, 2016

(54) METHOD FOR ENHANCING CATALYTIC ACTIVITY OF A LIPASE

(75) Inventors: Dhiren R. Thakker, Raleigh, NC (US); Ryan R. Klein, Raleigh, NC (US)

(73) Assignee: University of North Carolina at Chapel Hill, Chapel Hill, NC (US)

( * ) Notice: Subject to any disclaimer, the term of this patent is extended or adjusted under 35 U.S.C. 154(b) by 998 days.

(21) Appl. No.: 12/597,821

(22) PCT Filed: Apr. 28, 2008

(86) PCT No.: PCT/US2008/005486
§ 371 (c)(1),
(2), (4) Date: Feb. 26, 2010

(87) PCT Pub. No.: WO2008/134063
PCT Pub. Date: Nov. 6, 2008

(65) Prior Publication Data
US 2010/0330628 A1 Dec. 30, 2010

Related U.S. Application Data

(60) Provisional application No. 60/926,487, filed on Apr. 27, 2007.

(51) Int. Cl.
C12P 7/64 (2006.01)
C12N 9/20 (2006.01)

(52) U.S. Cl.
CPC . *C12P 7/649* (2013.01); *C12N 9/20* (2013.01); *Y02E 50/13* (2013.01); *Y02P 20/52* (2015.11)

(58) Field of Classification Search
None
See application file for complete search history.

(56) References Cited

U.S. PATENT DOCUMENTS

| 4,798,793 | A | 1/1989 | Eigtved | |
|---|---|---|---|---|
| 4,940,845 | A | 7/1990 | Hirota et al. | |
| 5,156,963 | A | 10/1992 | Eigtved | |
| 5,342,768 | A | 8/1994 | Pedersen et al. | |
| 5,697,986 | A | 12/1997 | Haas | |
| 5,713,965 | A | 2/1998 | Foglia et al. | |
| 5,776,741 | A | 7/1998 | Pedersen et al. | |
| 6,398,707 | B1 | 6/2002 | Wu et al. | |
| 6,642,399 | B2 | 11/2003 | Boocock | |
| 7,745,391 | B2 * | 6/2010 | Mintz et al. | 514/19.3 |
| 7,902,154 | B2 * | 3/2011 | Lee et al. | 514/15.1 |
| 2005/0176118 | A1 * | 8/2005 | Oakeshott et al. | 435/128 |

FOREIGN PATENT DOCUMENTS

| WO | WO 89/01032 | 2/1989 |
|---|---|---|
| WO | WO2008/134063 | 11/2008 |

OTHER PUBLICATIONS

Karageorgos et al. (Mol. BioSyst., 2010, vol. 6, pp. 1381-1388).*
Klien et al. (J. Biol. Chem., vol. 286, No. 14, 2011, pp. 12407-12416).*
Miller Ben-Avram, (PNAS, vol. 83., pp. 4185-4189, 1986).*
Jauhiainen et al. (JBC, vol. 263, No. 14, 1988, pp. 6525-6533).*
Basi et al. J. Mol. Catalysis B:Enzymatic, vol. 3 1997, pp. 171-176).*
Horowitz et al. (J. of General Physiol., 2005, pp. 243-262).*
Zvonok et al. (Chem. & Biol., vol. 15, pp. 854-862, 2008).*
Zaliha et al. (Appl. Biochem. & Biotech., vol. 118, pp. 1-20, 2004).*
Hsin-Ju et al. (J. Arg. Food. Chem., vol. 54, 2006, pp. 5777-5781).*
Mori et al. (Biotech. & Bioengin., vol. 76, No. 2, 2001, pp. 157-163).*
Feibt et al. (Molecular Pharmacology, vol. 67, No. 5, pp. 1751-1757).*
Heemskerk et al. (Biochimica et Biophysica Acta 1355, 1997, pp. 81-88).*
Horowitz et al. (J. of General Physiology, vol. 126, No. 3, Sep. 2005, pp. 243-262).*
Feibt et al. (Mol. Pharm., vol. 67, No. 5, pp. 1751-1757).*
Miyamoto et al. (Life Sciences, vol. 62, No. 17/18, pp. 1549-1553, 1998).*
Dutton et al. (PNAS, vol. 105, No. 33, pp. 11933-11938).*
Wilsher et al.(Drug Metabol. & Disposition, vol. 35, No. 7, pp. 1017-1022).*
Derewenda (1994). Structure and function of lipases. Adv Protein Chem. 45:1-52.
Lotti and Algberghina (2007). Lipases: Molecular Structure and Function, in J. Polaina and A. P. MacCabe (eds.) Industrial Enzymes, 263-281. Springer.
Lowe (1997). Structure and Function of Pancreatic Lipase and Colipase. Annu. Rev. Nutr. 17:141-58.
Mala & Takeuchi (2008). Understanding Structural Features of Microbial Lipases—An Overview. Analytical Chemistry Insights. 3: 9-19.
Reis et al.(2009). Lipases at Interfaces: A review. Adv Colloid Interface Sci. 147-148:237-50. Nestlé Research Center, CH-1000 Lausanne 26, Switzerland. doi: 10.1016/j.cis.2008.06.001. Epub Jul. 3, 2008.
Arpigny, J.L., and Jaeger, K., "Bacterial lipolytic enzymes: classification and properties," Biochem. J. vol. 343 pp. 177-183 (1999).
Cereijido et al., "The making of a tight junction," Journal of Cell Science. Suppl. 17 pp. 127-132 (1993).
Genbank® Accession No. CAA85776. Lagercrantz et al., "Genomic organization and complete cDNA sequence of the human phosphoinositide-specific phospholipase C beta 3 gene (PLCB3)," Genomics. vol. 26, No. 3 pp. 457-472 (1995).

(Continued)

*Primary Examiner* — Hope Robinson
(74) *Attorney, Agent, or Firm* — Jenkins, Wilson, Taylor & Hunt, P.A.

(57) ABSTRACT

Methods for enhancing a biological activity, for example, catalytic activity, of a lipase, are provided. In some embodiments, the methods include the step of alkylating one or more cysteine residues present within the lipase. Also provided are modified polypeptides for which a biological activity is enhanced by the disclosed methods, methods for using the disclosed polypeptides, including for the transesterification of renewable oils to produce a biofuel, and cell free systems that include a lipase, to which one or more moieties, such as steroidal moieties, are conjugated.

6 Claims, 9 Drawing Sheets

(56) References Cited

OTHER PUBLICATIONS

Genbank® Accession No. I38994. Sullivan et al., "IL-5 targeted ribozymes," U.S. Pat. No. 5,616,488 (Apr. 1, 1997).

Hama et al., "Biodiesel-fuel production in a packed-bed reactor using lipase-producing Rhizopus oryzae cells immobilized within biomass support particles," Biochemical Engineering Journal. vol. 34 pp. 273-278 (2007).

Hide et al., "Structure and evolution of the lipase superfamily," Journal of Lipid Research. vol. 33 pp. 167-178 (1992).

Hou et al., "In Vivo Activity of a Phospholipase C Inhibitor, 1-(6-((17β-3-Methoxyestra-1,3,5(10)-trien-17-yl)amino)hexyl)-1H-pyrrole-2,5-dione (U73122), in Acute and Chronic Inflammatory Reactions," The Journal of Pharmacology and Experimental Therapeutics. vol. 309, No. 2, pp. 697-704 (2003).

James et al., "Kinetic Analysis of Phospholipase Cβ Isoforms Using Phospholipid-Detergent Mixed Micelles," The Journal of Biological Chemistry. vol. 270, No. 20 pp. 11872-11881 (1995).

James et al., "Time-dependent inhibition of phospholipase Cβ-catalyzed phosphoinositide hydrolysis: a comparison of different assays," Biochem. J. vol. 314 pp. 917-921 (1996).

Ji et al., "Essential role of the tyrosine kinase substrate phospholipase C-γ1 in mammalian growth and development," PNAS. vol. 94, No. 7 pp. 2999-3003 (1997).

Jones et al., "PLCγγ1 is essential for early events in integrin signalling required for cell motility," Journal of Cell Science. vol. 118, No. 12 pp. 2695-2706 (2005).

Klein et al., "Direct Activation of Human Phospholipase Cβ3 in Dodecylmaltoside Mixed Micelles via Alkylation at Cysteine Residues," Poster (2007).

Klein et al., "Direct activation of human phospholipase cβ3 (hPLCβ3) by U73122 I dodecylmaltoside (DDM) mixed micelles via alkylation at cysteine residues," The FASEB Journal. vol. 21 p. 729.9 (2007) [Abstract].

Li et al., "Large-Scale Biodiesel Production From Microalga Chlorella protothecoides Through Heterotrophic Cultivation in Bioreactors," Biotechnology and Bioengineering. vol. 98, No. 4 pp. 764-771 (2007).

Mazuruk et al., "Structural Organization and Expression of the Human Phosphatidylinositol-Specific Phospholipase C β-3 Gene," Biochemical and Biophysical Research Communications. vol. 212, No. 1 pp. 190-195 (1995).

Morris et al., "A Receptor and G-protein-regulated Polyphosphoinositide-specific Phospholipase C from Turkey Erthrocytes," The Journal of Biological Chemistry. vol. 265, No. 23 pp. 13501-13507 (1990).

Notification Concerning Transmittal of International Preliminary on Patentability (Chapter I of the Patent Cooperation Treaty) corresponding to International Patent Application No. PCT/US2008/005486 dated Nov. 5, 2009.

Notification of Transmittal of the International Search Report and the Written Opinion of the International Searching Authority, or the Declaration corresponding to International Patent Application No. PCT/US2008/005486 dated Nov. 3, 2008.

Ranganathan et al., "An overview of enzymatic production of biodiesel," Bioresource Technology. vol. 99 pp. 3975-3981 (2008).

Rhee, S.G., and Choi, K.D., "Regulation of Inositol Phospholipid-specific Phospholipase C Isozymes," The Journal of Biological Chemistry. vol. 267, No. 18 pp. 12393-12396 (1992).

Thompson et al., "The Aminosteroid U-73122 Inhibits Muscarinic Receptor Sequestration and Phosphoinositide Hydrolysis in SK-N-SH Neuroblastoma Cells," The Journal of Biological Chemistry. vol. 266, No. 35 pp. 23856-12862 (1991).

Ward et al., "Phospholipase C-γ Modulates Epithelial Tight Junction Permeability through Hyperphosphorylation of Tight Junction Proteins," The Journal of Biological Chemistry. vol. 277, No. 38 pp. 35760-35765 (2002).

Ward et al., "Role of Phospholipase C-β in the Modulation Epithelial Tight Junction Permeability," The Journal of Pharmacology and Experimental Therapeutics. vol. 304, No. 2 pp. 689-698 (2003).

Alberts et al., Molecular Biology of the Cell. 4th edition. New York: Garland Science; 2002. Chapter 10: The Lipid Bilayer. Available from: http://www.ncbi.nlm.nih.gov/books/NBK26871/.

Oren et al., Biophysical J. (2004) 87, 768-779.

van Meer et al., Nature Reviews Molecular Cell Biology (2008) 9, 112-124.

* cited by examiner

METHOD FOR ENHANCING CATALYTIC ACTIVITY OF A LIPASE

RELATED APPLICATIONS

The presently disclosed subject matter claims the benefit of U.S. Provisional Patent Application Ser. No. 60/926,487, filed Apr. 27, 2007, the disclosure of which is incorporated herein by reference in its entirety.

TECHNICAL FIELD

The presently disclosed subject matter relates, in general, to methods for enhancing the biological activity of a lipase. More particularly, the presently disclosed subject matter relates to methods for modifying lipases to enhance the biological activities thereof, modified lipases activated by the disclosed methods, and methods for using the activated lipases, including for the transesterification of renewable oils to produce a biofuel.

BACKGROUND

The terms "biofuel" and "biofuel" refer to fatty acid monoesters made from oils comprising triacylglycerol lipids. Generally, biofuels are produced from oils such as soybean oil, linseed oil, sunflower oil, castor oil, corn oil, canola oil, rapeseed oil, palm kernel oil, cottonseed oil, peanut oil, coconut oil, palm oil, tung oil, and safflower oil, as well as derivatives thereof.

Several different methods are currently being used for producing biofuel from such starting materials. One such method involves hydrolyzing fatty acids from the triacylglycerol to form glycerol and free fatty acids. The free fatty acids are separated from the glycerol and reacted with a monohydric alcohol in the presence of a liquid phase acid catalyst to form the fatty acid monoester and water. The water is then removed to produce biofuel. This acid hydrolysis followed by esterification is chemically efficient, but the overall process requires two different chemical reactions and two different separations steps and is therefore not economically efficient.

Another method that can be used to make biofuel employs direct alcoholytic transesterification of the triacylglycerol with the monohydric alcohol to form the fatty acid monoester and glycerol, followed by separation of the fatty acid monoester from the glycerol. This method can be more efficient than the previous method because only a single reaction and single separation step need to be performed. However, maximum efficiency of the reaction typically requires the presence of a catalyst.

The most widely used catalyst is a liquid hydroxide, typically sodium hydroxide or potassium hydroxide dissolved in methanol to generate a methoxide ion, which is highly reactive. The amount of hydroxide catalyst required for efficient alcoholytic transesterification is at least 0.75% wt/vol hydroxide to methanol, and more typically about 1% to 5% wt/vol. Even at these amounts however, the reaction typically converts only about 80% of the triacylglycerols into fatty acid monoesters before reaching an equilibrium.

An additional method for producing biofuel involves the enzymatic transesterification of the triacylglycerol. For example, U.S. Pat. No. 5,713,965, the disclosure of which is incorporated herein in its entirety, describes a method that utilizes lipases to transesterify triglyceride-containing substances and to esterify free fatty acids to alkyl esters using short chain alcohols. Employing enzymatic transesterification for industrial scale production of biofuel suffers from several shortcomings, not the least of which is that the methanol that is employed as the acyl acceptor in the transesterification reaction inactivates the lipase, resulting in a reduced enzyme activity over time. Additionally, the process is limited by the activity of the enzyme itself.

What are needed, then, are new methods for increasing the efficiency of enzymatic transesterification of renewable oils to produce biofuel.

SUMMARY

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

Provided herein in some embodiments is a method for producing a biofuel, the method comprising: (a) providing a modified lipase; and (b) contacting the modified lipase with one or more biofuel reactants under conditions suitable to produce a biofuel. The method can comprise alkylating one or more cysteine residues present within the lipase. In some embodiments the lipase is modified to comprise a steroidal moiety.

Provided herein in some embodiments is a method for enhancing a biological (e.g., catalytic) activity of a lipase, the method comprising alkylating one or more cysteine residues present within the lipase, whereby the biological activity of the lipase is enhanced. In some embodiments, the lipase is modified to comprise a steroidal moiety. In some embodiments the biological (e.g., catalytic) activity of the lipase is enhanced two-, three-, four- or more-fold as compared to the corresponding lipase that has not been alkylated.

In some embodiments, provided herein is a system comprising a lipase comprising one or more steroidal moieties, optionally U73122 moieties or U73122 analog moieties, and a surface. In some embodiments, a biological activity of the lipase is enhanced relative to the same system in which the lipase does not comprise any such moieties. In some embodiments, the system is a cell-free system. In some embodiments, the surface is provided on a particle, sheet, plate, or the like.

In some embodiments, provided herein is an isolated modified lipase, comprising one or more steroidal moieties, optionally U73122 moieties or U73122 analog moieties. In some embodiments the one or more steroidal moieties, optionally U73122 moieties or U73122 analog moieties, are bound to one, two, three, four, five, six, seven, eight, or more cysteine residues present in the modified lipase. In some embodiments the one or more moieties are bound to one, two, three, four, five, six, seven, eight, or more cysteine residues corresponding to the cysteine residues set forth as C193, C221, C360, C516, C614, C892, C1176, and C1207 of SEQ ID NO: 1. In some embodiments the lipase comprises an amino acid sequence as set forth in SEQ ID NO: 1, or a functional fragment thereof, and further wherein at least one of C193, C221, C360, C516, C614, C892, C1176, and C1207, if present, is conjugated to a steroidal moiety, optionally a 073122 moiety or U73122 analog moiety.

In some embodiments, the lipase is selected from the group including but not limited to a *Thermomyces lanuginosus* lipase, a *Candida antarctica* Lipase B, a phospholipase C β, optionally a phospholipase C β3, and combinations thereof. In some embodiments, the phospholipase C β3 is a mammalian phospholipase C β3. In some embodiments, the mammalian phospholipase C β3 is a human phospholipase C β3 that comprises an amino acid sequence as set forth in SEQ ID NO: 1, or a biologically active fragment or variant thereof. In some embodiments, the one or more cysteine residues are selected from the group consisting of C193, C221, C360, C516, C614, C892, C1176, and C1207 of SEQ ID NO: 1. In some embodiments, the lipase is an avian phospholipase C β, optionally a turkey phospholipase C β comprising an amino acid sequence as set forth in SEQ ID NO: 2, or a biologically active fragment or variant thereof.

In some embodiments the lipase is present in a cell free system. In some embodiments, the cell free system comprises mixed micelles.

In some embodiments, the alkylating comprises contacting the lipase with an alkylating agent, optionally U73122 (1-(6-[((17β)-3-methoxyestra-1,3,5[10]-trien-17-yl)amino]hexyl]-2,5-pyrrolidinedione) or analog thereof, under conditions and for a time sufficient that at least one, optionally one to eight, cysteine residue(s) on the lipase is/are alkylated. In some embodiments, the lipase is bound to a surface.

It is thus an object of the presently disclosed subject matter to provide activated lipases and methods of use therefor.

An object of the presently disclosed subject matter having been stated hereinabove, and which is achieved in whole or in part by the presently disclosed subject matter, other objects will become evident as the description proceeds when taken in connection with the accompanying drawings as best described hereinbelow.

BRIEF DESCRIPTION OF THE DRAWINGS

In FIG. 10, n is in some embodiments between 0 and 20, inclusive.

BRIEF DESCRIPTION OF THE SEQUENCE LISTING

SEQ ID NO: 1 is an amino acid sequence of a human phospholipase C β3 (PLCβ3) gene product, and corresponds to GENBANK® Accession No. NP_000923, encoded by GENBANK® Accession No. NM_000932.

SEQ ID NO: 2 is an amino acid sequence of a turkey phospholipase C beta (PLCβ) gene product, and corresponds to GENBANK® Accession No. AAC60011, encoded by GENBANK® Accession No. U49431.

SEQ ID NO: 3 is an amino acid sequence of a lipase from *Thermomyces lanuginosus* and corresponds to GENBANK® Accession No. CAB58509, encoded by GENBANK® Accession No. A74251. This polypeptide is available in an immobilized form as LIPOZYME® TL IM (Novozymes, Bagsvaerd, Denmark).

SEQ ID NO: 4 is an amino acid sequence of a lipase B from *Candida antarctica* and corresponds to GENBANK® Accession No. CAA83122, encoded by GENBANK® Accession No. Z30645. This polypeptide is available in an immobilized form as NOVOZYME® 435 (NOVOZYMES™, Bagsvaerd, Denmark).

DETAILED DESCRIPTION

I. General Considerations

Phospholipase C is an important cellular regulatory lipase that catalyzes the hydrolysis of phosphatidylinositol-4,5-bisphosphate ($PIP_2$) into two cellular second messengers, inositol triphosphate ($IP_3$) and diacylglycerol (DAG), which modulate intracellular calcium concentrations and protein kinase C activity, respectively. To date, thirteen human PLC isozymes have been identified comprising six distinct and differentially regulated families (β1-4, γ1-2, δ1,3-4, ε, η1-2, and ζ; Harden & Sondek, 2006). They exhibit relatively low overall sequence similarity, even within isozyme families, but all contain conserved catalytic core domains designated as X and Y boxes. It is therefore not surprising that all PLC isozymes act predominantly on two substrates: $PIP_2$ and PIP, with some catalytic activity towards PI (Rhee & Choi, 1992). The major differences between isozymes of different families are directly reflected in their specific modes of regulation. PLCβ and γ isozymes are the most well studied, and are directly coupled to cell surface receptors (i.e., heterotrimeric G-protein coupled receptors and receptor tyrosone kinases respectively) that serve to regulate their activity. Signaling pathways involving PLC isozymes are implicated in a number of critical cellular functions such as motility (Jones et al., 2005), growth and differentiation (Ji et al., 1997), as well as in the assembly and regulation of tight junctions (Balda et al., 1991; Cereijido et al., 1993; Ward et al., 2002; Ward et al., 2003).

Figure 1:
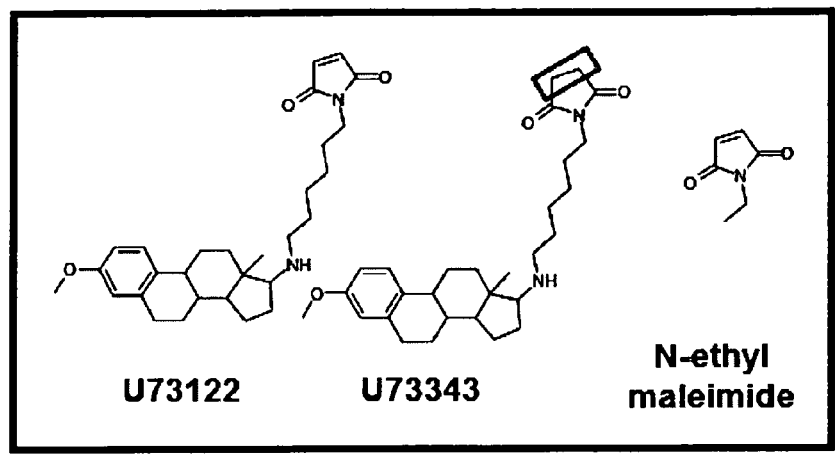
FIG. 1 shows the chemical structures of 1-(6-[((17β)-3-methoxyestra-1,3,5[10]-trien-17-yl)amino]hexyl]-2,5-pyrrolidinedione (U73122), 1-[6-[[17β-3-methoxyestra-1,3,5 (10)-trien-17yl]amino]-2-5-pyrrolidine-dione (U73343), and N-ethylmaleimide (NEM).

U73122 ((1-(6-[((17β)-3-methoxyestra-1,3,5[10]-trien-17-yl)amino]hexyl]-2,5-pyrrolidinedione); see FIG. 1) is an aminosteroid first reported as an inhibitor of PLC dependent process (Bleasdale et al., 1989). Additional reports have since indicated that several isozymes of PLC are inhibited by U73122, but not by the close structural analog, U73343 (Smith et al, 1990; Hou et al., 2003; Carvou et al., 2007). This has also been shown in both MDCK and Caco-2 cells, as U73122 inhibits ATP-stimulated PLC activity in both cells lines in a concentration dependent manner, while the closely related compound U73343 (see FIG. 1) does not (Ward et al., 2003). U73122 has been shown to inhibit phospholipase C (PLC) activity in a concentration dependent manner in a number of cell culture models.

Disclosed herein are assessments of the ability of a representative alkylating agent to modulate lipase activity in a cell free system, and also identification of the mechanism underlying the interaction of U73122 with these enzymes using cell free enzyme activity assays and mass spectrometry. A goal of this work was to evaluate the direct interaction between U73122 and a representative lipase in a cell free system. PLC activity was assessed by measuring changes in [$^3$H]-inositol phosphate formation following incubation of purified hPLCβ3 with phosphatidylinositol-4,5-bisphosphate in a dodecylmaltoside (DDM) micellar system. Mass spectrometry of intact hPLCβ3 was performed on an Agilent LCMSD-TOF while peptide sequencing of digested protein was performed on an ABI-QSTAR. Surprisingly, U73122 was found to increase the activity of hPLCβ3 in DDM mixed micelles in a concentration and time dependent manner ($EC_{50}$=14±5 µM). This activation was inhibited by glutathione ($IC_{50}$=38±16 µM) suggesting covalent modification of cysteine residues on the enzyme. Mass spectrometric analysis of U73122-activated hPLCβ3 confirmed alkylation at up to eight cysteine residues on the full length protein, specifically identified by LC/MS/MS peptide sequencing.

This finding is potentially applicable to all or many lipases as an approach to increase biological activities of these enzymes. A modified lipase with increased enzymatic activity could lead to greater sensitivity and reduced use of reagents during processes that rely on lipase biological activities. For example, lipases are also often used as catalysts in biochemical reactions. Use of a lipase with an increased activity is expected to reduce the amount of lipase required to catalyze a specific reaction, which can lead to an overall less expensive small or large scale production of desirable product. A modified lipase thus represents a novel biocatalyst in the field of enzymology.

II. Definitions

While the following terms are believed to be well understood by one of ordinary skill in the art, the following definitions are set forth to facilitate explanation of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art. While the following terms are believed to be well understood by one of ordinary skill in the art, the following definitions are set forth to facilitate explanation of the presently disclosed subject matter.

Following long-standing patent law convention, the terms "a", "an", and "the" mean "one or more" when used in this application, including the claims.

The term "about", as used herein when referring to a measurable value such as an amount of weight, time, dose (e.g., radiation dose), etc. is meant to encompass in some embodiments variations of ±20% or ±10%, in some embodiments ±5%, in some embodiments ±1%, in some embodiments ±0.1%, and in some embodiments ±0.01% from the specified amount, as such variations are appropriate to perform the disclosed methods.

As used herein, the terms "biofuel" and "biodiesel" refer to fatty acid monoesters made from oils comprising triacylglycerol lipids. As such, these terms relate in some embodiments to ester-based fuel oxygenates derived from biological sources and intended for use in compression-ignition engines (see e.g., National Soy Diesel Development Board, 1994).

III. Methods of Modifying Lipases

In some embodiments, the presently disclosed subject matter relates to the discovery that alkylation of a representative lipase, human phospholipase C β3 (hPLCβ3), with an in vivo (cellular) inhibitor thereof, resulted in an increase in the biological activity of hPLCβ3 in a cell free system. Exemplary lipases include, but are not limited to phospholipases, optionally phospholipases A, B, C, or D. Numerous lipases are known to one of ordinary skill in the art, and the disclosure of the exemplary lipases set forth in SEQ ID NOs: 1-4 is not intended to imply that these lipases are the only lipases appropriate for use in the presently disclosed subject matter. Functional fragments, analogs, and/or derivates of the lipases are also with the scope of the presently disclosed subject matter.

As disclosed herein, the in vivo (cellular) inhibitor U73122 modulates hPLCβ3 biological activity in cell free systems. It has been further found that exposure to U73122 results in conjugation of U73122 moieties to hPLCβ3 at several cysteine residues. In the amino acid sequence of hPLCβ3 set forth in SEQ ID NO: 1, there are a total of 14 cysteine residues, 8 of which were found to be conjugated to U73122.

This finding suggests that U73122 and/or other thiol alkylating agents with appropriate physical-chemical properties that promote interactions with lipid micellar systems can enhance one or more biological activities (e./g., a catalytic activity) when conjugates of the lipases and U73122 and/or such other alkylating agents are prepared and allowed to interact with lipase substrates in cell free systems (e.g., with lipid bilayers and/or micelles).

Accordingly, in some embodiments the presently disclosed subject matter provides methods for enhancing a biological activity of a lipase, the method comprising alkylating one or more cysteine residues present within the phospholipase, whereby the biological activity of the phospholipase is enhanced. In some embodiments, the lipase is a phospholipase Cβ, preferably a phospholipase Cβ3. In some embodiments, the phospholipase Cβ3 is a mammalian phospholipase Cβ3, and in some embodiments the mammalian phospholipase β3 is a human phospholipase Cβ3 that comprises an amino acid sequence as set forth in SEQ ID NO: 1, or a biologically active fragment or variant thereof. In some embodiments, the lipase is an avian lipase, for example, a turkey phospholipase Cβ having an amino acid sequence as set forth in SEQ ID NO: 2, or a biologically active fragment or variant thereof. It is noted, however, that other lipases, including such industrially important lipases as those set forth in SEQ ID NOs: 3 and 4 as well as derivatives thereof including, but not limited to LIPOZYME® TL IM and NOVOZYME® 435 (both produced by NOVOZYMES™, Bagsvaerd, Denmark), can also be modified by alkylation.

The alkylation of the lipases can occur at any position, with the proviso that the modification does not destroy the enzymatic action of the lipase. In some embodiments, the alkylation reaction results in the conjugation of a moiety (e.g., steroidal moieties, such as but not limited to U73122 moieties or analogs thereof) to one or more cysteine amino acids present within the primary structure of the lipase. In some embodiments, the one or more cysteine residues are selected from the group including, but not necessarily limited to C193, C221, C360, C516, C614, C892, C1176, and C1207 of SEQ ID NO: 1, or the cysteine residues that correspond to these cysteine residues in other lipases from humans or other species.

In some embodiments, the alkylating step comprises contacting the lipase with an alkylating agent (e.g., an akylating agent comprising a steroidal moiety, such as but not limited to U73122 moieties or analogs thereof) under conditions and for a time sufficient that in some embodiments at least one or more, in some embodiments three or more, and in some embodiments eight cysteine residue(s) on the phospholipase is/are alkylated.

Thus, as set forth herein, the methods of the presently disclosed subject matter relate in some embodiments to modifications of lipases that result in an enhancement of a biological (e.g., catalytic) activity of the lipases relative to the unmodified lipases upon which the modified lipases are based. In some embodiments, the biological (e.g., catalytic) activity of the lipase is enhanced two-, three-, four- or more-fold as compared to the corresponding lipase that has not been alkylated.

In some embodiments, the lipases of the presently disclosed subject matter are present in a cell free system. In some embodiments, a cell free system comprises a lipid layer, for example liposomes, micelles, etc. In some embodiments, the cell free system comprises dodecylmaltoside (DDM) mixed micelles. Thus, the presently disclosed subject matter provides in some embodiments cell free systems comprising a lipase to which one or more moieties (e.g., steroidal moieties, such as but not limited to U73122 moieties or analogs thereof) are conjugated. In some embodiments, the lipase is a mammalian phospholipase Cβ3. In some embodiments, a biological activity of the lipase to which one or more moieties (e.g., steroidal moieties, such as but not limited to U73122 moieties or analogs thereof) are conjugated is enhanced relative to the same cell free system in which the lipase is not conjugated to any such moieties. In some embodiments, the lipid structure comprises a micelle, which in some embodiments comprises a mixed micelle.

The presently disclosed subject matter thus also provides isolated modified lipases. In some embodiments, the isolated modified lipase comprises one or more moieties (e.g., steroidal moieties, such as but not limited to U73122 moieties or analogs thereof) conjugated thereto. In some embodiments, the one or more moieties (e.g., steroidal moieties, such as but not limited to U73122 moieties or analogs thereof) are conjugated to one, two, three, four, five, six, seven, eight, or more cysteine residues present in the modified lipase. In some embodiments, the one or more moieties (e.g., steroidal moieties, such as but not limited to U73122 moieties or analogs thereof) are conjugated to one, two, three, four, five, six, seven, eight, or more cysteine residues corresponding to the cysteine residues set forth as C193, C221, C360, C516, C614, C892, C1176, and C1207 of SEQ ID NO: 1, which presents the amino acid sequence of GENBANK® Accession No. NP_000923 (i.e., human phospholipase C, β3 (phosphatidylinositol-specific). In some embodiments, the lipase comprises an amino acid sequence as set forth in SEQ ID NO: 1, or a functional fragment thereof, and further wherein at least one of C193, C221, C360, C516, C614, C892, C1176, and C1207, if present, is conjugated to a moiety (e.g., steroidal moieties, such as but not limited to U73122 moieties or analogs thereof).

Given the enhanced activities of the modified polypeptides of the presently disclosed subject matter, the presently disclosed subject matter also provides isolated biocatalysts comprising a lipase to which one or more moieties (e.g., steroidal moieties, such as but not limited to U73122 moieties or analogs thereof) are conjugated. In some embodiments, the biocatalysts permit production and/or isolation of chemical compounds (e.g., enantiomers) more readily and/or in better yield than would be possible via synthetic methods. In some embodiments, the lipase polypeptide comprises an amino acid sequence as set forth in SEQ ID NO: 1, and the one or more moieties (e.g., steroidal moieties, such as but not limited to U73122 moieties or analogs thereof) are conjugated to one or more cysteine residues selected from the group consisting of C193, C221, C360, C516, C614, C892, C1176, and C1207.

Agents for modifying a lipase in accordance with the presently disclosed subject matter include agents comprising alone or in combination: an akylating moiety, a steroidal moiety, and a linker moiety. Examples of such moieties are provided in the Examples herein below, and other examples would be apparent to one of ordinary skill in the art upon a review of the instant disclosure.

IV. Exemplary Lipases

As set forth hereinabove, an exemplary lipase comprises an amino acid sequence as set forth in SEQ ID NO: 1. Additional exemplary lipases include, but are not limited to lipases comprising amino acids sequences as set forth in SEQ ID NOs: 2-4, or biologically active fragments and derivatives thereof. As used herein, the phrase "biologically active" refers to a polypeptide, fragment, analog or derivative thereof that retains at least a fraction of a biological activity (e.g., a catalytic activity) of a naturally occurring polypeptide upon which it is based. In the case of lipases, a biologically active lipase, fragment, analog or derivative thereof is capable in some embodiments of catalyzing the transesterification of a fatty acid to a monoester thereof, such as by a reaction scheme as follows:

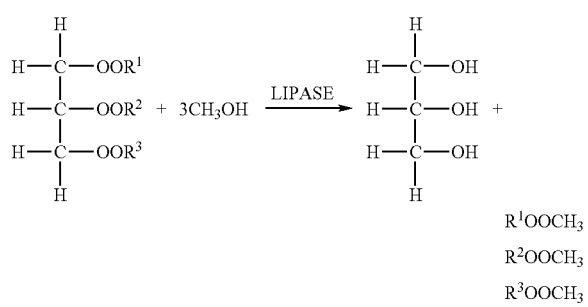

in which $OOR^1$, $OOR^2$, and $OOR^3$ are individually the same or different fatty acid chains and $R^1OOCH_3$, $R^2OOCH_3$, and $R^3OOCH_3$ are the corresponding methyl esters thereof generated by transesterification using methanol as an acyl acceptor. It is noted, however, that methanol is not the only acyl acceptor that can be employed, and other acyl acceptors including, but not limited to ethanol, 1-propanol, and 1-butanol can also be employed in a transesterification reaction catalyzed by a lipase.

Additional lipases that can be employed in the compositions and methods of the presently disclosed subject matter are known to those of skill in the art and include, but are not limited to the lipases disclosed in GENBANK® Accession Nos. AAZ31460, BAG16821, P19515, A34959, B34959, CAA00250, P22088, ABN09945, A39133, AAC60402, and P41773, as well as biologically active fragments and derivatives thereof. The contents of these GENBANK® Accession Nos., including all annotations therein, are incorporated by reference herein in their entireties.

As set forth in U.S. Pat. No. 5,697,986, additional lipases include LIPOSYM™ IM 20, *Rhizomucor miehei* lipase immobilized on a Duolite resin (Novo Nordisk BioChem, Franklinton, N.C., United States of America); lipase CE, derived from *Humicola lanuginosa*; and lipase PS-30, derived from *Pseudomonas* sp. (both obtained from Amano Enzyme U.S.A. Co., Ltd., Troy, Va., United States of America).

Lipases to be modified in accordance with the presently disclosed subject matter can comprise free and accessible cysteine residues that do not have another function crucial for enzyme activity. By way of example and not limitiation, an alkylating agent can modify the lipase on free and accessible cysteine residues within the protein sequence. However, it is also possible to modify residues are within the active site. The alkylated protein now has a number of highly lipophilic moieties hanging off it, particularly steroidal moieties. The lipophilicity of the steroidal moieties provides a mechanism for the modified protein to preferentially interact with a lipid substrate, which can be present in a micelle, for example. While it is not desired to be bound by any particular theory of operation, this interaction is believed to keep the protein in close proximity with its substrate and leads to an increase in the number of substrate molecules that are cleaved by the lipase (increased activity).

V. Methods of Producing a Biofuel

The presently disclosed subject matter also relates to methods for producing a biofuel. In some embodiments, the methods comprise (a) providing a modified lipase; and (b) contacting the modified lipase with one or more biofuel reactants under conditions suitable to produce a biofuel.

As used herein, the phrase "biofuel reactants" refers to compositions that when contacted with a modified lipase of the presently disclosed subject matter under appropriate reaction conditions results in the generation of a biofuel by transesterification of one or more of the biofuel reactants by the modified lipase. Exemplary biofuel reactants include fatty acid-containing substances such as oils, which in the presence of alcohols can be transesterified with a modified lipase of the presently disclosed subject matter. Exemplary fatty acid-containing substances that have been successfully employed for the production of biofuels include sunflower oil (Mittelbach, 1990), rapeseed oil (Linko et al., 1994), soybean oil, and beef tallow (Lazar, 1985). These reactions generally involve the use of primary alcohols, although transesterifications with secondary alcohols have also been disclosed (see e.g., Shaw et al., 1991).

Generally, transesterification processes are carried out by forming a reaction mixture by combining the starting materials (i.e., fatty-acid containing substances and alcohol), modified lipase, solvent, and sufficient water to confer enzymatic activity, incubating the reaction mixture for a time and at a temperature sufficient for the reaction (i.e., transesterification between the fatty acid-containing substance and the alcohol) to occur and separating the undesirable end products (glycerol, water, and modified lipase, with the modified lipase optionally being recovered and re-purified) from the alkyl ester-containing biofuel portion of the reaction mixture. Water is optionally included in the reaction mixture as needed to confer enzymatic activity on the catalyst. This amount can be easily determined experimentally by one of skill in the art. The reaction is generally carried out at about room temperature, however, slightly elevated temperatures (up to about 60° C.) can also produce acceptable levels of enzyme activity.

The amount of incubation time considered effective can vary from one enzyme/substrate combination to another. This amount is easily determined experimentally, however, by carrying out time course experiments. Starting materials are fatty acid-containing substances (i.e., biofuel reactants) and alcohol. Acceptable fatty acid-containing substances are triglycerides, phospholipids, and other materials which are substrates for the particular enzyme chosen as catalyst. Acceptable alcohols are generally, but not limited to, those of the normal-, iso- and cyclo-series of alkyl alcohols. Examples are ethanol, propanol, isopropanol, 1-butanol, 2-butanol and isobutanol. Since higher molecular weight alcohols are more soluble in automotive fuels, they are generally more useful. Alcohol limitations are dictated by the choice of enzyme to be used as catalyst, since some will accept only primary alcohols while others will accept primary as well as secondary ones.

The solvent is in some embodiments automotive and related fuels and includes diesel fuel, gasoline, and similar materials. Effective lipases are any produced by plants, bacteria, fungi or higher eukaryotes. In general, the use of non-specific enzymes results in the production of a higher yield than fatty acid-specific enzymes. In the event that the esters of particular fatty acids are desired or particular fatty acid-containing substances are used as substrate, lipases having particular fatty acid specificities may be preferred. Ester production occurs directly in the fuel, eliminating isolation and purification prior to blending. End by-products (glycerol, water, and enzyme) can be separated from the biofuel by conventional methods such as settling and phase separation.

EXAMPLES

The following Examples provide illustrative embodiments. In light of the present disclosure and the general level of skill in the art, those of skill will appreciate that the following Examples are intended to be exemplary only and that numerous changes, modifications, and alterations can be employed without departing from the scope of the presently disclosed subject matter.

Example 1

PLCβ3 Activity by Cell Free Assay

Purified human PLCβ3 protein was generously provided by the laboratory of Dr. T. K. Harden (Department of Pharmacology, University of North Carolina, Chapel Hill, N.C., United States of America). The activity of PLCβ3 in a cell free system was evaluated by an adaptation of previously published methods (James et al., 1995; James et al., 1996). Briefly, hot and cold phosphatidylinositol-4,5-bisphosphate ($PIP_2$; 5 nmol), as substrate, was reconstituted in a 1 mM dodecylmaltoside solution and mixed with assay buffer containing 40 mM Hepes (pH 7.4), 480 mM KCl, 40 mM NaCl, 8 mM EGTA, 4 mM $MgCl_4$, and 7.6 mM $CaCl_2$. Compounds at desired concentrations and purified PLCβ3 in 1% fatty acid-free BSA and 10 mM Hepes (pH 7.0), were subsequently added to the mixture. To initiate assays, samples were moved to a 37° C. water bath and incubated for 2-10 minutes such that less than fifteen percent total substrate was hydrolyzed. At designated times, reactions were stopped by addition of 750 µl $CHCl_3$:MeOH:HCl (40:80:1), 100 µl water, 250 µl $CHCl_3$, and 250 µl 0.1M HCl. Samples were vortexed and centrifuged at 3000 rpm for 10 minutes at 4° C. The amount of formed [$^3$H]-inositol phosphates was measured by liquid scintillation counting of 500 µl of the upper phase in a Packard Tri Carb 4000 Series spectrophotometer.

Example 2

Mass Spectrometry

Mass spectrometry of intact PLCβ3 was performed using reversed-phase chromatography coupled to on an Agilent (Santa Clara, Calif., United States of America) LC-MSD-TOF mass spectrometer (Wagner et al., 2007). The mass-to-charge data were transformed to the mass domain using Bio-Confirm software from Agilent. For peptide sequencing, solution phase and SDS gel bands of unmodified and modified PLCβ3 was incubated with trypsin overnight at 37° C. (Mosely et al., 2001). The tryptic peptides were subsequently analyzed by nano-LC/MS/MS using a Dionex UltiMate nano LC (Sunnyvale, Calif., United States of America) coupled to Sciex (Toronto, Ontario, Canada) Q-Star Pulsar i mass spectrometer. The results were processed using MASCOT (Matrix Sciences, Boston, Mass., United States of America) protein database that had the mass of U73122 modification created as a variable modification.

Example 3

Data Analysis

Data are expressed as mean±SD of three experiments performed in triplicate unless otherwise indicated. Statistical significance was evaluated using unpaired Students t tests. Data were modeled using Win-non Lin (Pharsight, Mountain View, Calif., United States of America) non-linear regression analysis for determination of $EC_{50\ (PLC\beta3)}$ and $IC_{50}$ values.

Examples 4-6

Design and Synthesis of U73122 Analogs as Inhibitors of PLC-β Isozymes and Enhancers of Tight Junction Permeability

Rationale

U73122 is a potent inhibitor of PLC-β in cells and tissue as described previously (Thompson et al., 1991) and demonstrated herein. U73122 also enhances tight junction permeability in MDCK and Caco-2 cell monolayers in a concentration-dependent fashion, and that the potency of U73122 as an enhancer of tight junction permeability is comparable to its potency as a PLC inhibitor in the same cell system. These studies suggested that the effect of U73122 on tight junction permeability is mediated via inhibition of PLC-β isozymes. This Example provides several potent inhibitors of PLC-β isozymes by designing and synthesizing structural analogs of U73122 with respect to the steroid moiety, the alkyl linker and the maleimide and other functionality. The potent PLC-β inhibitors identified through these studies are expected to be potent enhancers of tight junction permeability. The mode of PLC-β inhibition by U73122 is not known. While it is not desired to be bound by any particular theory of operation, it is suspected that the alkylating agent (e.g., maleimide moiety) is modifying a catalytically important nucleophile (e.g., sulfhydryl group) on PLC. This Example evaluates this mechanism. This Example also addresses the identification of potent reversible inhibitors of PLC-β with a transient effect on tight junction permeability. Finally, this Example also examines if U73122 and its analogs have inhibitory activity toward PLC-β isozymes, and if so, whether inhibitory potency toward PLC-β isozymes is related to their potency as enhancers of tight junction permeability.

Example 4

Analogs of U73122 with Variations in the Steroid Functionality

Figure 9:
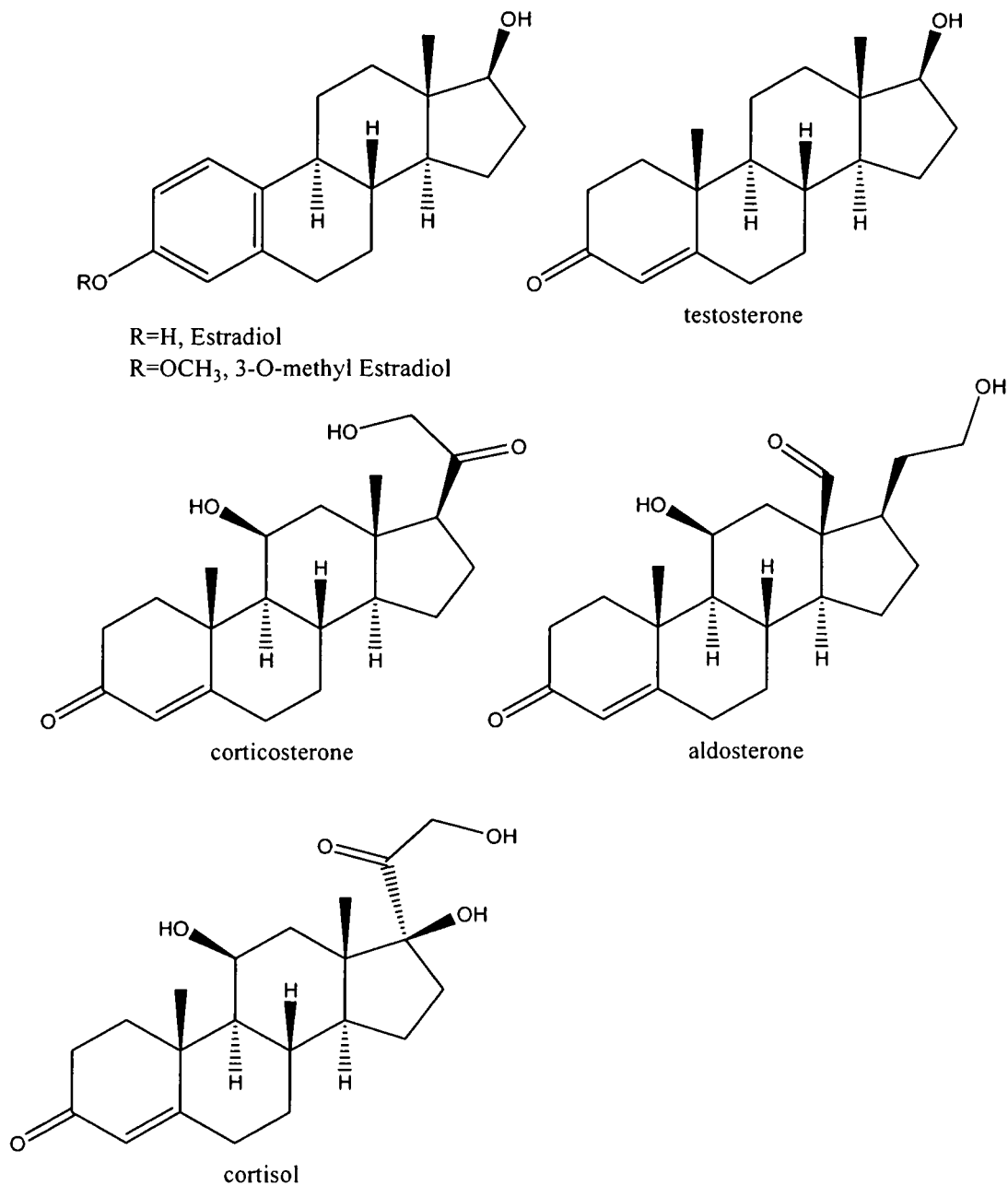
FIG. 9 depicts the chemical structures of steroid moieties that can be functionalized at C-17, for example, to produce analogs of U73122 as per Scheme A.

The steroid moieties are shown in Scheme A (FIG. 9) as examples of the steroids that can be functionalized on their C-17 substituents, for example, with an alkylating moiety to produce U73122 analogs as inhibitors of PLC-β. An exemplary structure of a modified U73122 is shown immediately below. After initial evaluation of these compounds, further structure-activity relationship is pursued centered on the steroid functionality. By way of particular example and not limitation, the alcohol functionality on the C-17 substituents can be linked to alkylating moiety via an ester linkage or an ether linkage using synthetic procedures established in the art.

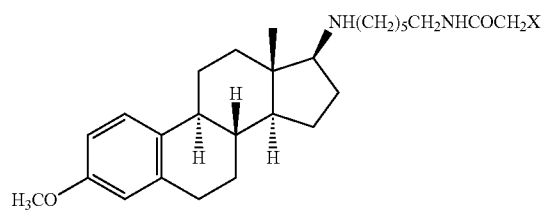

wherein X=halo (e.g., I, Br, Cl).

Example 5

Figure 10:
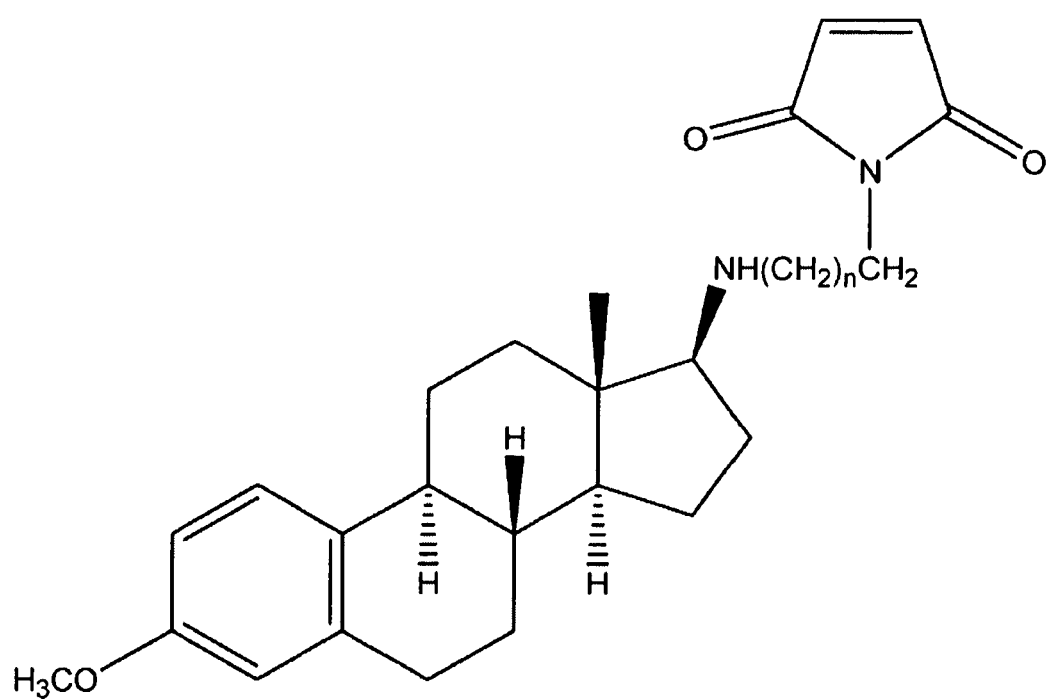
FIG. 10 depicts the chemical structures of U73122 analogs with varying alkyl chain linker between the steroid and maleimide moieties as per Scheme B.

U73122 Analogs with Varying Alkyl Chain Linkers Between the Steroid and the Maleimide Moieties Several derivatives of U73122 are synthesized in which the alkyl chain linker between the steroid and the maleimide moieties are varied in length. Representative examples are shown in Scheme B (see FIG. 10). N-(chloroalkyl) maleimides are prepared with varying alkyl chain lengths, and these are condensed with the aminosteroid functionality by synthetic procedures established in the art.

Example 6

Evaluation of U73122 Analogs

Inhibition of PLC-β in the Cell Free System:

The effects of each inhibitor on PLC-β activity is determined in vitro with isolated PLC isozymes. This approach with isolated enzymes provides a clean system in which to evaluate the specificity of the inhibitors on PLC isozyme activity directly, and attempts to confirm or refute the reported selectivity of these inhibitors for specific PLC isozymes determined in whole cell assays. PLC-β iszoymes that are expressed in Caco-2 cells are purified following expression in cultured insect cells using recombinant baculovirus as described previously (Paterson et al., 1997). Subsequently, inhibition of the activity of isolated PLC-β is assessed by previously published methods (Morris et al., 1990; Paterson et al., 1997).

Briefly, hot and cold $PIP_2$ (5 nmol) as substrate is reconstituted in a 1% cholate solution with inhibitors at desired concentrations. Assay buffer containing 40 mM Hepes (pH 7.4), 480 mM KCl, 40 µM NaCl, 8 mM EGTA, 23.2 mM $MgSO_4$, and 8.4 mM $CaCl_2$ and purified PLC-β in 1% fatty acid-free BSA and 10 mM Hepes (pH 7.0) are then added to the substrate/inhibitor mixture. To initiate assays, samples are moved to 30° C. water bath and incubated for 10 minutes. Reactions are stopped by addition of 10% TCA and 10 mg/ml fatty acid free BSA. Samples are then vortexed and centrifuged at 3000 rpm for 10 minutes at 4° C. The amount of formed [$^3$H]-inositol phosphates is measured by liquid scintillation counting in a Packard Tri Carb 4000 Series spectropholometer.

Inhibition of PLC-β in Cell Monolayers:

ATP selectively activates PLCβ via activation of G-protein coupled receptors (e.g., $P2Y_2$ receptor; Inoue, 1997). Thus, inhibition of PLC-β is assessed in cell preparations that have been pretreated with ATP. The activation of PLC-β isozyme renders the contribution of enzymatic activity from other isozymes insignificant, and thus allows assessment of inhibitory activity toward this particular isozyme. The inhibitory potency of a compound is estimated by comparing PLC activity after activation with ATP in the absence or presence of the putative inhibitor. Potency for inhibition of PLC isozymes can be defined by the concentration of the compound to decrease the activity of PLC-β isozyme by 50% ($IC_{50\ (PLC-\beta)}$).

Briefly, inhibition of the activity of PLCβ in cell monolayers is determined by an adaptation of a previously published method (Schachter et al., 1997). Cells are seeded at 60,000 or 100,000 cells/well (Caco-2 cells and MDCK cells, respectively) in a 12-well transwell and subsequently cultured for 21 or 4 days. Cell monolayers are then labeled with [$^3$H]-myo-inositol (2 µCi/well in 2 ml of inositol-free media (0.5 ml in apical chamber and 1.5 ml in basolateral chamber) for 24 hours at 37° C. Labeled cells are removed from the incubator, media is aspirated and cells are washed 2× with transport buffer (HBSS supplemented with 10 mM HEPES and 25 mM glucose), and incubated for 30 minutes at 37° C. Assays are initiated by replacing apical buffer with fresh buffer containing PLC inhibitor at desired concentrations and incubating for 30 minutes at 37° C. Buffer in both chambers will then be replaced with fresh buffer containing 50 mM LiCl and 300 µM ATP to stimulate PLC-β activity, and incubating for 15 minutes at 37° C. to allow accumulation of [$^3$H]-inositol phosphates. Incubations are terminated by aspiration of the media, excision of filters, and the addition of 1 ml of boiling 10 mM EDTA (pH 8.0) to centrifuge tubes containing the excised filters. The supernatant is applied to AG1 X8 formate columns for chromatographic isolation of [$^3$H]-inositol phosphates (Berridge et al., 1983). The amount of [$^3$H]-inositol phosphates is measured by liquid scintillation counting in a Packard Tri Carb 4000 Series spectrophotometer. Data from each experiment is normalized to the response observed with 300 µM ATP and is reported as the mean±SD of three experiments performed in triplicate.

Discussion of the Examples

U73122 has long been used as an inhibitor of phospholipase C (PLC) in cellular and biochemical assays. The structural analog U73343 has been reported as inactive towards PLC, suggesting a role for the maleimide moiety on U73122 in the observed inhibition. A purpose of the studies disclosed herein was to directly evaluate the interaction between U73122 and hPLCβ3 in a cell free assay.

Figure 2:
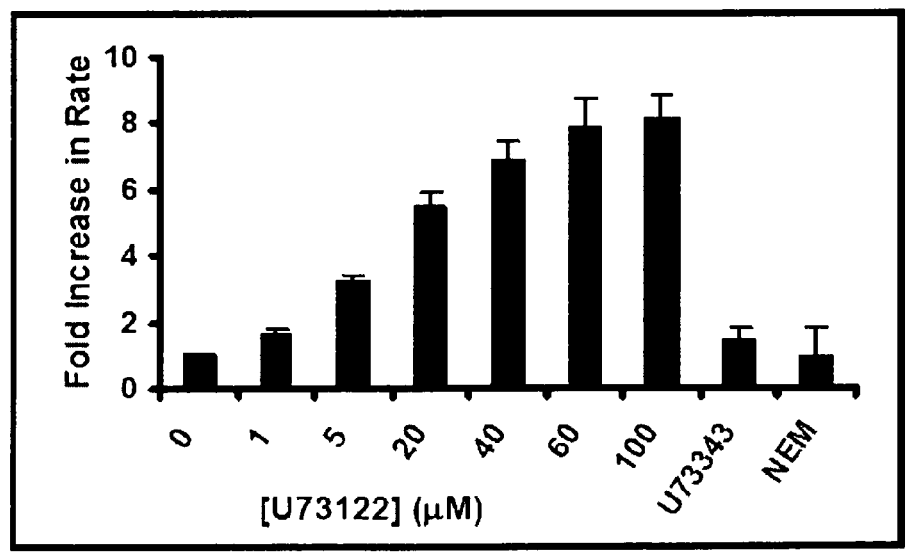
FIG. 2 is a bar graph showing that U73122 but not the structurally related molecules U73343 and NEM, increases the activity of human phospholipase C β3 (hPLCβ3) in dodecylmaltoside (DDM) mixed micelles. In contrast to the results obtained in cellular assays, U73122 increases the activity of hPLCβ3 in DDM mixed micelles, while structurally related molecules U73343 and NEM, do not.
Figure 3:
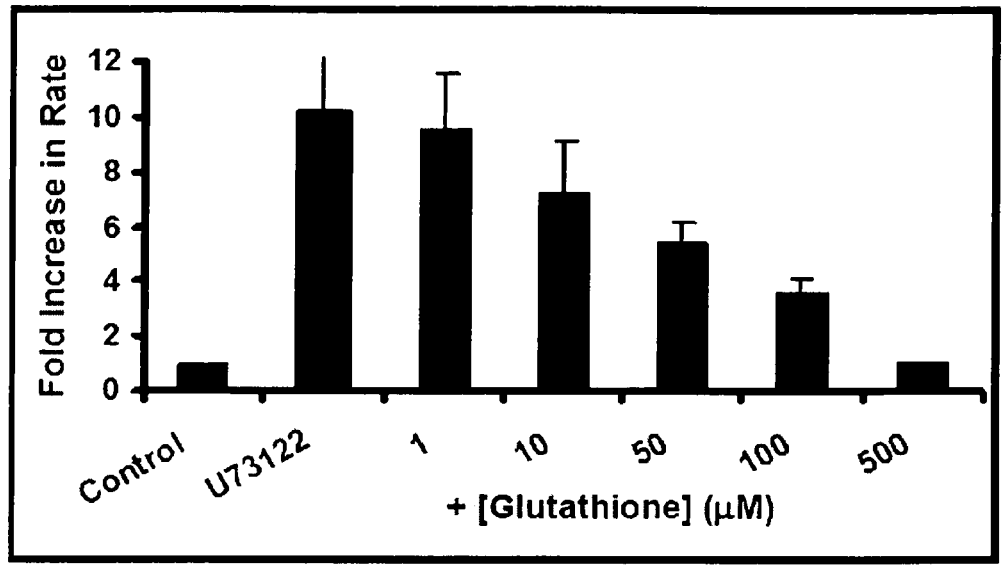
FIG. 3 is a bar graph showing that the thiol containing nucleophile glutathione (GSH) inhibits the U73122-induced activation of hPLCβ3, suggesting that the maleimide moiety plays a role in the observed activation. Thiol containing nucleophiles, GSH and cysteine (data for cysteine not shown) inhibit the U73122 induced activation of hPLCβ3 suggesting that the maleimide moiety plays a role in the observed activation.
Figure 4:
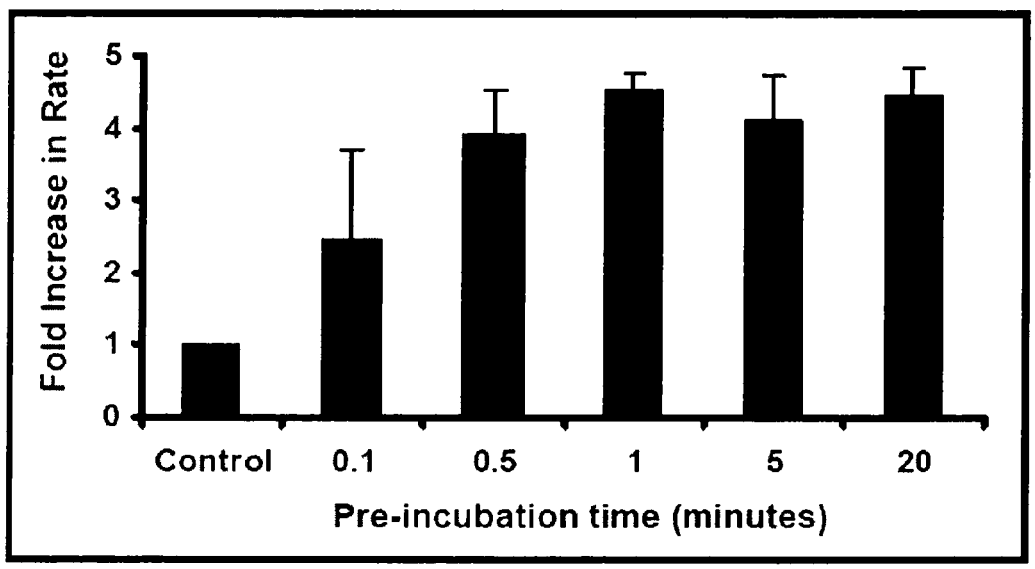
FIG. 4 is a bar graph showing that activation of hPLCβ3 by U73122 is time dependent, which suggests an irreversible or at least slowly reversible mechanism.
Figure 5A:
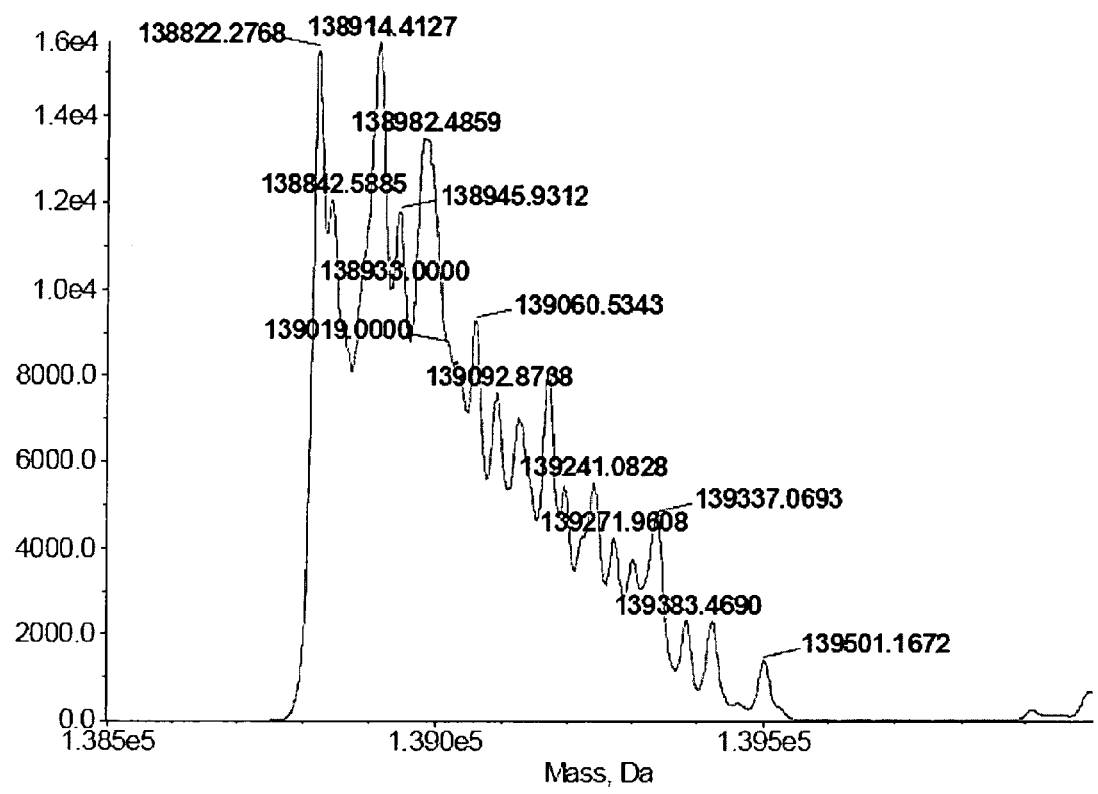
FIGS. 5A and 5B are mass spectra plots showing apo-hPLCβ3 with an expected mass of about 138 kDa (FIG. 5A) and that incubation with U73122 in DDM mixed micelles led to an increase in the observed molecular weight of hPLCβ3 consistent with the covalent addition of up to eight U73122 molecules (FIG. 5B).
Figure 5B:
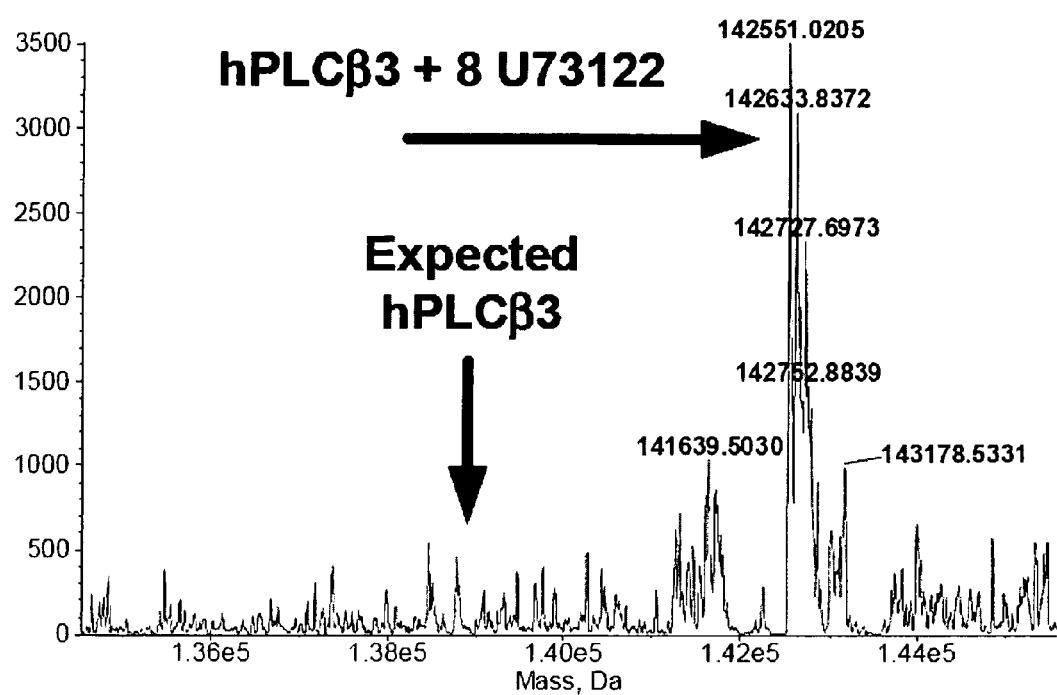
Figure 6A:
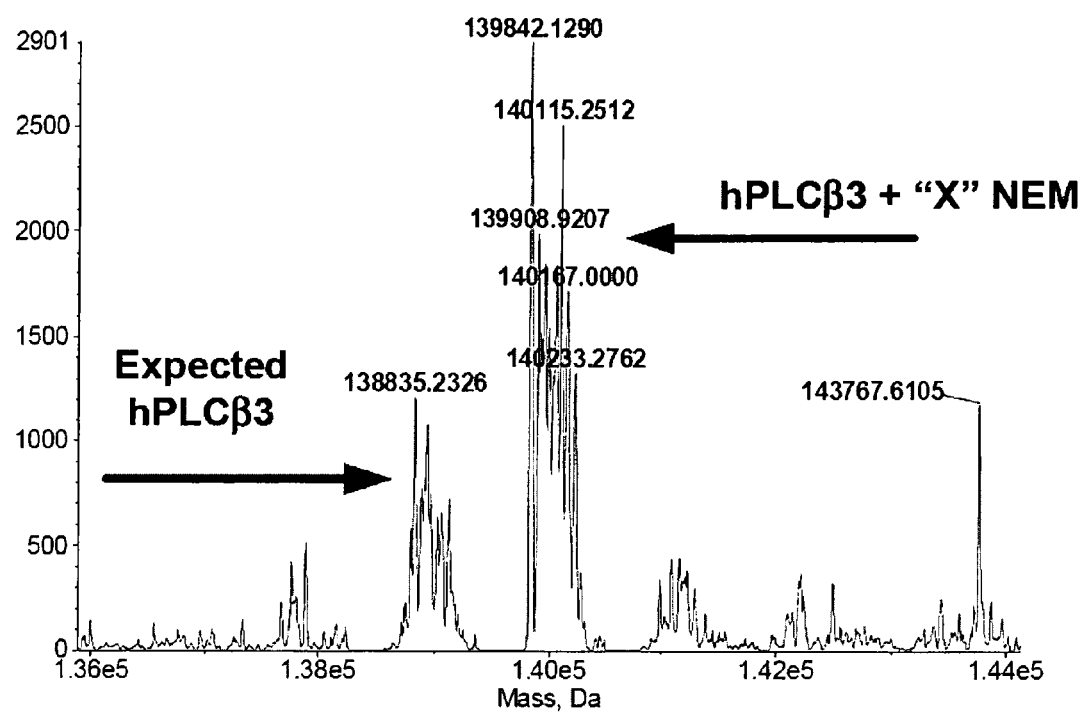
FIGS. 6A and 6B are a plot and bar graph, respectively, showing that NEM alkylates hPLCβ3 at multiple amino acid residues (FIG. 6A) and that despite its inability to activate hPLCβ3 in DDM mixed micelles, NEM inhibits the U73122 induced activation of hPLCβ3 (FIG. 6B), which suggesting alkylation of the same amino acid residues. * indicates 20 minute pre-incubation.
Figure 6B:
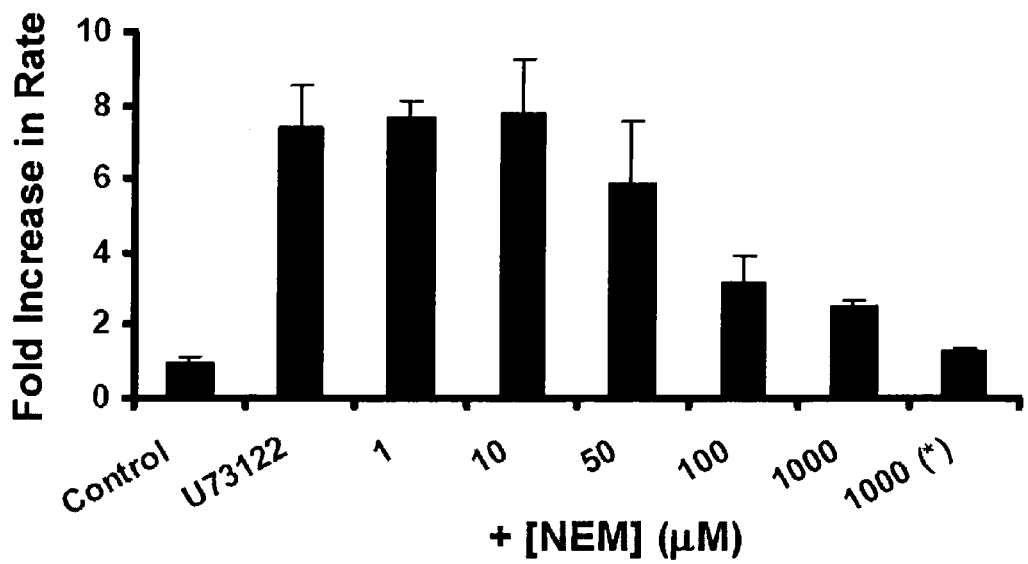

The PLC inhibitor, U73122, inhibits PLC activity in a concentration dependent manner in two cell culture models of intestinal epithelia: MDCK and Caco-2 cells. Disclosed herein is the evaluation of the interaction between U73122 and PLC in a cell free system. PLC activity was assessed by measuring changes in [$^3$H]-inositol phosphate formation following incubation of purified hPLCβ3 with phosphatidylinositol-4,5-bisphosphate in a DDM micellar system. Mass spectrometry of intact hPLCβ3 was performed on an Agilent LCMSD-TOF while peptide sequencing of digested protein was performed on an ABI-QSTAR. Surprisingly, U73122 was found to increase the activity of hPLCβ3 in DDM mixed micelles in a concentration and time dependent manner (see FIG. 2; $EC_{50}=14\pm5$ µM). Activation was inhibited by glutathione (see FIG. 3; $IC_{50}=38\pm16$ µM) suggesting covalent modification of cysteine residues on the enzyme. Mass spectrometric analysis of U73122-activated hPLCβ3 confirmed alkylation at up to eight cysteine residues, specifically identified by LC/MS/MS peptide sequencing (see FIGS. 5A, 5B, 7, and 8).

Figure 7:
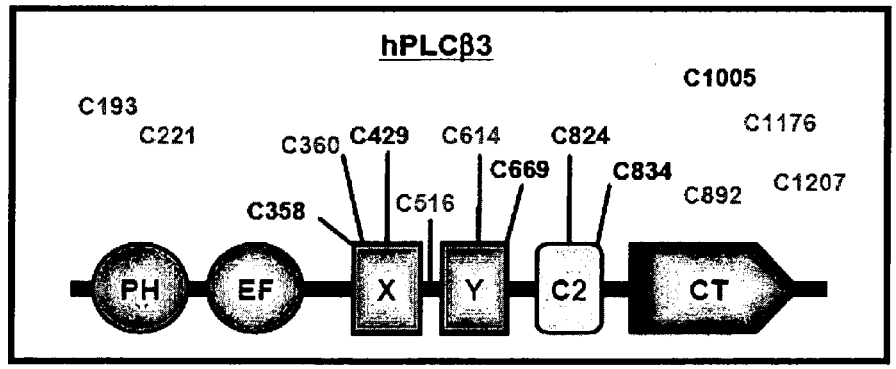
FIG. 7 is a representation of the structure of the hPLCβ3 polypeptide, showing the location of the 14 cysteine residues in hPLCβ3. Eight of these residues were identified as alkylated by U73122 following incubation in DDM mixed micelles (i.e., C193, C221, C360, C516, C614, C892, C1176, and C1207). PH—pleckstrin homology domain; EF—flexible linker domain; X—X box; Y—Y box; C2—C2 domain; CT—caboxy-terminal domain. LC/MS/MS peptide mapping of protease digested protein identified 12 of 14 total cysteine residues in hPLCβ3 (all except C669 and C834)).
Figure 8A:
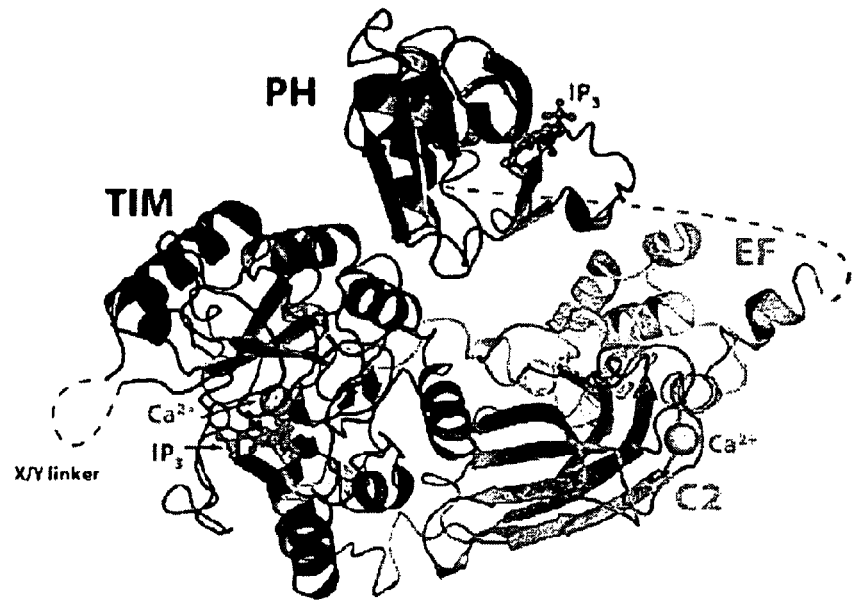
FIGS. 8A and 8B depict exemplary unmodified and modified lipases (hPLCβ3) of the presently disclosed subject matter, respectively.
Figure 8B:
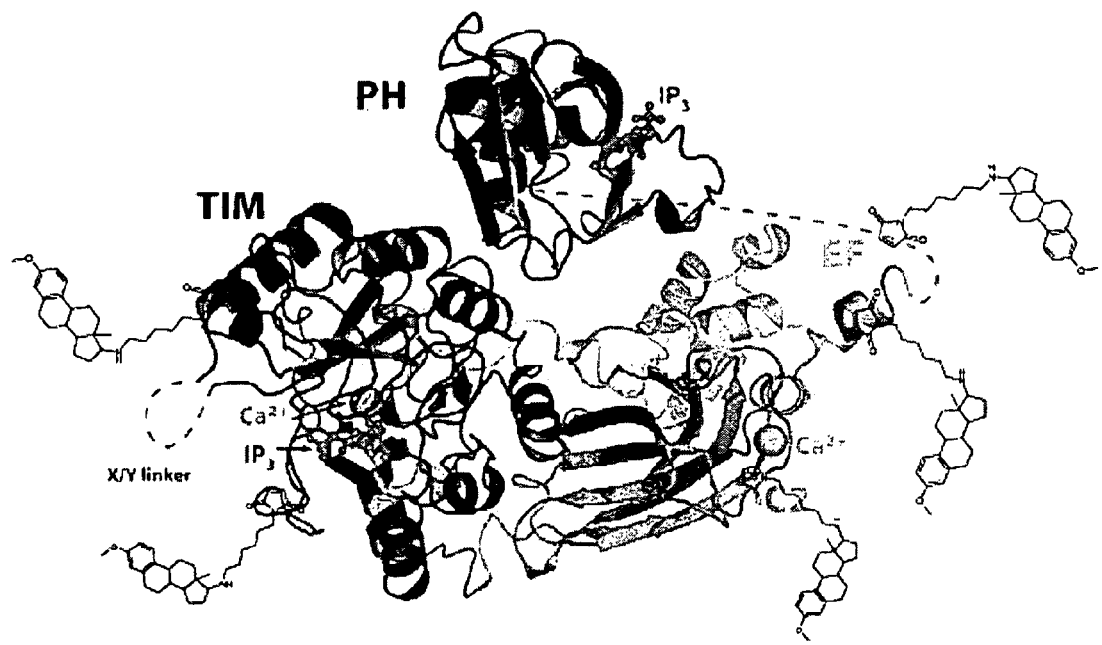

Collectively, these data suggest that U73122 increases the activity of hPLCβ3 in DDM mixed micelles via alkylation at up to eight cysteine residues (see FIGS. 7 and 8). While the instant co-inventors do not wish to be bound by any particular theory of operation, it is possible that covalent attachment of lipophilic U73122 facilitates the interaction between PLC and substrate leading to increased activity. For example, it is possible that U73122 serves as lipid anchor for hPLCβ3 promoting association of the enzyme with the substrate interface and subsequently increasing lipase activity.

REFERENCES

The references listed below as well as all references cited in the specification, including patents, patent applications, journal articles, and all database entries (e.g., GENBANK® Accession Nos., including any annotations presented in the GENBANK® database that are associated with the disclosed sequences), are incorporated herein by reference to the extent that they supplement, explain, provide a background for, or teach methodology, techniques, and/or compositions employed herein.

Balda et al., (1991) *J Memb Biol*. 122(3):193-202.
Berridge et al. (1983) *Biochem J* 212:473-482.
Bleasdale et al., (1989) *Adv Prost Throm Leukot Res.* 19:590-593.
Carvou et al., (2007) *Cell Signal*. 19(1):42-51.
Cereijido et al., (1993) *J Cell Sci Suppl.* 17:127-132.
GENBANK® Accession Nos. A34959; A39133; A74251; AAC60011; AAC60402; AAZ31460; ABN09945; B34959; BAG16821; CAA00250; CAA83122; CAB58509; NM_000932; NP_000923; P19515; P22088; P41773; U49431; Z30645.
Harden & Sondek (2006) *Ann Rev Pharmacol Toxicol.* 46:355-379.
Horowitz et al., (2005) *J Gen Physiol*. 126(3):243-262.
Hou et al., (2003) *J Pharmacol Exp Ther* 309(2):697-704.
Inoue (1997) *Nippon Yakurigaku Zasshi* 110:173-182.
James et al., (1995) *J Biol Chem.* 270(20):11872-11881
James et al., (1996) *Biochem J.* 314:917-921.
Ji et al., (1997) *Proc Natil Acad Sci USA* 94:2999-3003.
Jones et al., (2005) *J Cell Sci*. 118(12):2695-2706.
Linko et al. (1994) *J Am Oil Chem Soc* 71:1411-1414.
Lazar (1985) *Fette Seifen Anstrichm* 87:394-400.
Mittelbach (1990) *J Am Oil Chem Soc* 67:168-170.
Morris et al. (1990) *J Biol Chem* 265:13501-13507.
Mosely et al., (2001) Characterization of Proteins and Peptides by Mass Spectrometry. American Society for Mass Spectrometry Short Course, Chicago, Ill., United States of America.
National Soy Diesel Development Board (1994) *Biodiesel: A Technology, Performance, and Regulatory Overview*. Jefferson City, Mo., United States of America.
Paterson et al. (1997) *in Signaling by Inositol Lipids and Inositol Phosphates*, Shears (ed.) Oxford University Press, Oxford, United Kingdom, pages 85-98.
PCT International Patent Application Publication No. WO 89/01032.
Rhee & Choi (1992) *J Biol Chem.* 267(18):12393-12396.
Schachter et al. (1997) *Neuropharm* 36:1181-1187.
Shaw et al. (1991) *Enzyme Microb Technol* 13:544-546.
Smith et al., (1990) *J Pharmacol Toxicl*. 253(2):688-697.
Thompson et al. (1991) *J Biol Chem* 266:23856-12862.
U.S. Pat. Nos. 4,798,793; 4,940,845 5,156,963; 5,342,768; 5,697,986; 5,713,965; 5,776,741; 6,398,707; 6,642,399.
Wagner et al., (2007) *J Mass Spec* 42:139-149.
Ward et al., (2002) *J Biol Chem*. 277(38):35760-35765.
Ward et al., (2003) *J Pharmacol Exp Ther* 304:689-698.

It will be understood that various details of the presently disclosed subject matter may be changed without departing from the scope of the presently disclosed subject matter. Furthermore, the foregoing description is for the purpose of illustration only, and not for the purpose of limitation.

---

What is claimed is:

1. A method for enhancing a catalytic activity of a mammalian phospholipase Cβ3 comprising the amino acid sequence of SEQ ID NO: 1, the method comprising: (a) providing a mammalian phospholipase Cβ3 comprising the amino acid sequence of SEQ ID NO: 1; and (b) alkylating one or more cysteine residues selected from the group consisting of C193, C221, C360, C516, C614, C892, C1176, and C1207 of SEQ ID NO: 1 present within the mammalian phospholipase Cβ3 with a U73122 (1-(6-[((17β)-3-methoxyestra-1,3,5[10]-trien-17-yl)amino]hexyl]-2,5-pyrrolidinedione), whereby the catalytic activity of the mammalian phospholipase Cβ3 is enhanced.

2. The method of claim 1, wherein the mammalian phospholipase Cβ3 is present in a cell free system.

3. The method of claim 2, wherein the cell free system comprises mixed micelles.

4. The method of claim 1, wherein the mammalian phospholipase Cβ3 is bound to a surface.

5. The method of claim 1, wherein the alkylating step comprises contacting the mammalian phospholipase Cβ3 with U73122 under conditions and for a time sufficient such that cysteine residues C193, C221, C360, C516, C614, C892, C1176, and C1207 of SEQ ID NO: 1 on the mammalian phospholipase Cβ3 are alkylated.

6. The method of claim 1, wherein the catalytic activity of the mammalian phospholipase Cβ3 is enhanced two-, three-, four- or more-fold as compared to the corresponding mammalian phospholipase Cβ3 that has not been alkylated.

* * * * *

SEQUENCE LISTING

```
<160> NUMBER OF SEQ ID NOS: 4

<210> SEQ ID NO 1
<211> LENGTH: 1234
<212> TYPE: PRT
<213> ORGANISM: Homo sapiens

<400> SEQUENCE: 1

Met Ala Gly Ala Gln Pro Gly Val His Ala Leu Gln Leu Glu Pro Pro
1               5                   10                  15

Thr Val Val Glu Thr Leu Arg Arg Gly Ser Lys Phe Ile Lys Trp Asp
            20                  25                  30

Glu Glu Thr Ser Ser Arg Asn Leu Val Thr Leu Arg Val Asp Pro Asn
        35                  40                  45

Gly Phe Phe Leu Tyr Trp Thr Gly Pro Asn Met Glu Val Asp Thr Leu
    50                  55                  60

Asp Ile Ser Ser Ile Arg Asp Thr Arg Thr Gly Arg Tyr Ala Arg Leu
65                  70                  75                  80

Pro Lys Asp Pro Lys Ile Arg Glu Val Leu Gly Phe Gly Gly Pro Asp
                85                  90                  95

Ala Arg Leu Glu Glu Lys Leu Met Thr Val Val Ser Gly Pro Asp Pro
            100                 105                 110

Val Asn Thr Val Phe Leu Asn Phe Met Ala Val Gln Asp Asp Thr Ala
        115                 120                 125

Lys Val Trp Ser Glu Glu Leu Phe Lys Leu Ala Met Asn Ile Leu Ala
    130                 135                 140

Gln Asn Ala Ser Arg Asn Thr Phe Leu Arg Lys Ala Tyr Thr Lys Leu
145                 150                 155                 160

Lys Leu Gln Val Asn Gln Asp Gly Arg Ile Pro Val Lys Asn Ile Leu
                165                 170                 175
```

```
Lys Met Phe Ser Ala Asp Lys Lys Arg Val Glu Thr Ala Leu Glu Ser
                180                 185                 190

Cys Gly Leu Lys Phe Asn Arg Ser Glu Ser Ile Arg Pro Asp Glu Phe
                195                 200                 205

Ser Leu Glu Ile Phe Glu Arg Phe Leu Asn Lys Leu Cys Leu Arg Pro
210                 215                 220

Asp Ile Asp Lys Ile Leu Leu Glu Ile Gly Ala Lys Gly Lys Pro Tyr
225                 230                 235                 240

Leu Thr Leu Glu Gln Leu Met Asp Phe Ile Asn Gln Lys Gln Arg Asp
                245                 250                 255

Pro Arg Leu Asn Glu Val Leu Tyr Pro Pro Leu Arg Pro Ser Gln Ala
                260                 265                 270

Arg Leu Leu Ile Glu Lys Tyr Glu Pro Asn Gln Gln Phe Leu Glu Arg
                275                 280                 285

Asp Gln Met Ser Met Glu Gly Phe Ser Arg Tyr Leu Gly Gly Glu Glu
                290                 295                 300

Asn Gly Ile Leu Pro Leu Glu Ala Leu Asp Leu Ser Thr Asp Met Thr
305                 310                 315                 320

Gln Pro Leu Ser Ala Tyr Phe Ile Asn Ser Ser His Asn Thr Tyr Leu
                325                 330                 335

Thr Ala Gly Gln Leu Ala Gly Thr Ser Ser Val Glu Met Tyr Arg Gln
                340                 345                 350

Ala Leu Leu Trp Gly Cys Arg Cys Val Glu Leu Asp Val Trp Lys Gly
                355                 360                 365

Arg Pro Pro Glu Glu Glu Pro Phe Ile Thr His Gly Phe Thr Met Thr
370                 375                 380

Thr Glu Val Pro Leu Arg Asp Val Leu Glu Ala Ile Ala Glu Thr Ala
385                 390                 395                 400

Phe Lys Thr Ser Pro Tyr Pro Val Ile Leu Ser Phe Glu Asn His Val
                405                 410                 415

Asp Ser Ala Lys Gln Gln Ala Lys Met Ala Glu Tyr Cys Arg Ser Ile
                420                 425                 430

Phe Gly Asp Ala Leu Leu Ile Glu Pro Leu Asp Lys Tyr Pro Leu Ala
                435                 440                 445

Pro Gly Val Pro Leu Pro Ser Pro Gln Asp Leu Met Gly Arg Ile Leu
                450                 455                 460

Val Lys Asn Lys Lys Arg His Arg Pro Ser Ala Gly Gly Pro Asp Ser
465                 470                 475                 480

Ala Gly Arg Lys Arg Pro Leu Glu Gln Ser Asn Ser Ala Leu Ser Glu
                485                 490                 495

Ser Ser Ala Ala Thr Glu Pro Ser Ser Pro Gln Leu Gly Ser Pro Ser
                500                 505                 510

Ser Asp Ser Cys Pro Gly Leu Ser Asn Gly Glu Glu Val Gly Leu Glu
                515                 520                 525

Lys Pro Ser Leu Glu Pro Gln Lys Ser Leu Gly Asp Glu Gly Leu Asn
                530                 535                 540

Arg Gly Pro Tyr Val Leu Gly Pro Ala Asp Arg Glu Asp Glu Glu Glu
545                 550                 555                 560

Asp Glu Glu Glu Glu Gln Thr Asp Pro Lys Lys Pro Thr Thr Asp
                565                 570                 575

Glu Gly Thr Ala Ser Ser Glu Val Asn Ala Thr Glu Glu Met Ser Thr
                580                 585                 590

Leu Val Asn Tyr Ile Glu Pro Val Lys Phe Lys Ser Phe Glu Ala Ala
```

-continued

```
            595                 600                 605
Arg Lys Arg Asn Lys Cys Phe Glu Met Ser Ser Phe Val Glu Thr Lys
610                 615                 620

Ala Met Glu Gln Leu Thr Lys Ser Pro Met Glu Phe Glu Tyr Asn
625                 630                 635                 640

Lys Gln Gln Leu Ser Arg Ile Tyr Pro Lys Gly Thr Arg Val Asp Ser
                    645                 650                 655

Ser Asn Tyr Met Pro Gln Leu Phe Trp Asn Val Gly Cys Gln Leu Val
                660                 665                 670

Ala Leu Asn Phe Gln Thr Leu Asp Val Ala Met Gln Leu Asn Ala Gly
                675                 680                 685

Val Phe Glu Tyr Asn Gly Arg Ser Gly Tyr Leu Leu Lys Pro Glu Phe
690                 695                 700

Met Arg Arg Pro Asp Lys Ser Phe Asp Pro Phe Thr Glu Val Ile Val
705                 710                 715                 720

Asp Gly Ile Val Ala Asn Ala Leu Arg Val Lys Val Ile Ser Gly Gln
                    725                 730                 735

Phe Leu Ser Asp Arg Lys Val Gly Ile Tyr Val Glu Val Asp Met Phe
                740                 745                 750

Gly Leu Pro Val Asp Thr Arg Arg Lys Tyr Arg Thr Arg Thr Ser Gln
                755                 760                 765

Gly Asn Ser Phe Asn Pro Val Trp Asp Glu Glu Pro Phe Asp Phe Pro
770                 775                 780

Lys Val Val Leu Pro Thr Leu Ala Ser Leu Arg Ile Ala Ala Phe Glu
785                 790                 795                 800

Glu Gly Gly Lys Phe Val Gly His Arg Ile Leu Pro Val Ser Ala Ile
                    805                 810                 815

Arg Ser Gly Tyr His Tyr Val Cys Leu Arg Asn Glu Ala Asn Gln Pro
                820                 825                 830

Leu Cys Leu Pro Ala Leu Leu Ile Tyr Thr Glu Ala Ser Asp Tyr Ile
                835                 840                 845

Pro Asp Asp His Gln Asp Tyr Ala Glu Ala Leu Ile Asn Pro Ile Lys
850                 855                 860

His Val Ser Leu Met Asp Gln Arg Ala Arg Gln Leu Ala Ala Leu Ile
865                 870                 875                 880

Gly Glu Ser Glu Ala Gln Ala Gly Gln Glu Thr Cys Gln Asp Thr Gln
                    885                 890                 895

Ser Gln Gln Leu Gly Ser Gln Pro Ser Ser Asn Pro Thr Pro Ser Pro
                900                 905                 910

Leu Asp Ala Ser Pro Arg Arg Pro Gly Pro Thr Thr Ser Pro Ala
                915                 920                 925

Ser Thr Ser Leu Ser Ser Pro Gly Gln Arg Asp Asp Leu Ile Ala Ser
930                 935                 940

Ile Leu Ser Glu Val Ala Pro Thr Pro Leu Asp Glu Leu Arg Gly His
945                 950                 955                 960

Lys Ala Leu Val Lys Leu Arg Ser Arg Gln Glu Arg Asp Leu Arg Glu
                    965                 970                 975

Leu Arg Lys Lys His Gln Arg Lys Ala Val Thr Leu Thr Arg Arg Leu
                980                 985                 990

Leu Asp Gly Leu Ala Gln Ala Gln Ala Glu Gly Arg Cys Arg Leu Arg
                995                 1000                1005

Pro Gly Ala Leu Gly Gly Ala Ala Asp Val Glu Asp Thr Lys Glu
            1010                1015                1020
```

Gly Glu Asp Glu Ala Lys Arg Tyr Gln Glu Phe Gln Asn Arg Gln
    1025            1030            1035

Val Gln Ser Leu Leu Glu Leu Arg Glu Ala Gln Val Asp Ala Glu
    1040            1045            1050

Ala Gln Arg Arg Leu Glu His Leu Arg Gln Ala Leu Gln Arg Leu
    1055            1060            1065

Arg Glu Val Val Leu Asp Ala Asn Thr Thr Gln Phe Lys Arg Leu
    1070            1075            1080

Lys Glu Met Asn Glu Arg Glu Lys Lys Glu Leu Gln Lys Ile Leu
    1085            1090            1095

Asp Arg Lys Arg His Asn Ser Ile Ser Glu Ala Lys Met Arg Asp
    1100            1105            1110

Lys His Lys Lys Glu Ala Glu Leu Thr Glu Ile Asn Arg Arg His
    1115            1120            1125

Ile Thr Glu Ser Val Asn Ser Ile Arg Arg Leu Glu Glu Ala Gln
    1130            1135            1140

Lys Gln Arg His Asp Arg Leu Val Ala Gly Gln Gln Gln Val Leu
    1145            1150            1155

Gln Gln Leu Ala Glu Glu Pro Lys Leu Leu Ala Gln Leu Ala
    1160            1165            1170

Gln Glu Cys Gln Glu Gln Arg Ala Arg Leu Pro Gln Glu Ile Arg
    1175            1180            1185

Arg Ser Leu Leu Gly Glu Met Pro Glu Gly Leu Gly Asp Gly Pro
    1190            1195            1200

Leu Val Ala Cys Ala Ser Asn Gly His Ala Pro Gly Ser Ser Gly
    1205            1210            1215

His Leu Ser Gly Ala Asp Ser Glu Ser Gln Glu Glu Asn Thr Gln
    1220            1225            1230

Leu

<210> SEQ ID NO 2
<211> LENGTH: 1211
<212> TYPE: PRT
<213> ORGANISM: Meleagris gallopavo

<400> SEQUENCE: 2

Met Ser Met Leu Thr Pro Val Leu Gln Pro Pro Glu Val Lys Glu Tyr
1               5                   10                  15

Leu Ser Arg Gly Glu Arg Phe Ile Lys Trp Asp Asp Glu Thr Ala Ser
                20                  25                  30

Ala Ser Pro Val Ile Leu Arg Val Asp Pro Lys Gly Phe Tyr Leu Tyr
            35                  40                  45

Trp Thr Tyr Gln Asn Lys Glu Met Glu Ile Leu Asp Ile Thr Ser Ile
        50                  55                  60

Arg Asp Thr Arg Val Gly Arg Phe Ala Lys Ile Pro Lys Cys Gln Lys
65                  70                  75                  80

Leu Arg Glu Val Phe Asn Leu Asp Tyr Pro His Ser Thr Phe Leu Leu
                85                  90                  95

Lys Thr Leu Thr Ile Val Ser Gly Pro Asp Met Val Asp Leu Thr Phe
            100                 105                 110

His Asn Phe Val Ser Tyr Lys Glu Asn Val Gly Lys Ser Trp Ala Glu
        115                 120                 125

Asp Ile Met Ala Ile Val Gln Asn Pro Leu Thr Tyr Asn Ala Ser Arg
    130                 135                 140

```
Tyr Thr Phe Leu Glu Lys Ile Leu Val Lys Leu Lys Met Gln Leu Asn
145                 150                 155                 160

Ala Glu Gly Lys Ile Pro Val Arg Asn Ile Phe Gln Met Phe Pro Ala
                165                 170                 175

Asp Arg Lys Arg Val Glu Ala Ala Leu Asn Ala Cys His Leu Pro Lys
            180                 185                 190

Gly Lys Asn Asp Ala Ile Asn Pro Glu Asp Phe Pro Glu Thr Val Tyr
        195                 200                 205

Lys Thr Phe Leu Met Asn Leu Cys Pro Arg Pro Glu Ile Asp Glu Ile
    210                 215                 220

Phe Thr Ser His His Phe Lys Ala Lys Pro Tyr Met Thr Lys Glu His
225                 230                 235                 240

Leu Ala Lys Phe Ile Asn Lys Lys Gln Arg Asp Ser Arg Leu Asn Asp
                245                 250                 255

Ile Leu Phe Pro Pro Ala Lys Pro Glu Gln Val Gln Ser Leu Ile Glu
            260                 265                 270

Lys Tyr Glu Pro Ser Val Ile Asn Ile Gln Arg Gly Gln Leu Ser Pro
        275                 280                 285

Glu Gly Met Val Trp Phe Leu Cys Gly Pro Glu Asn Asn Val Ile Ala
    290                 295                 300

Leu Asp Lys Leu Val Leu Tyr Gln Asp Met Thr Gln Pro Leu Ser His
305                 310                 315                 320

Tyr Phe Ile Asn Ser Ser His Asn Thr Tyr Leu Thr Ala Gly Gln Phe
                325                 330                 335

Ser Gly Ile Ser Ser Pro Glu Met Tyr Arg Gln Thr Leu Leu Ala Gly
            340                 345                 350

Cys Arg Cys Val Glu Leu Asp Cys Trp Lys Gly Arg Pro Pro Asp Glu
        355                 360                 365

Glu Pro Ile Ile Thr His Gly Phe Thr Met Thr Glu Ile Leu Phe
    370                 375                 380

Lys Asp Ala Ile Glu Ala Ile Ala Glu Ser Ala Phe Lys Thr Ser Leu
385                 390                 395                 400

Tyr Pro Val Ile Leu Ser Phe Glu Asn His Val Asp Ser Pro Lys Gln
                405                 410                 415

Gln Ala Lys Met Ala Glu Tyr Cys Arg Thr Ile Phe Gly Asp Met Leu
            420                 425                 430

Leu Thr Glu Pro Leu Glu Lys Tyr Pro Leu Lys Pro Gly Val Pro Leu
        435                 440                 445

Pro Ser Pro Lys Asp Leu Leu Gly Lys Ile Leu Ile Lys Asn Lys Lys
    450                 455                 460

Lys Gln Phe Val Ser Lys Arg Gln Ser Ser Met Lys Lys Gly Lys
465                 470                 475                 480

Asn Val Glu Pro Glu Ile Ile Glu Gln Pro Ala Phe Thr Asp Ala Glu
                485                 490                 495

Asp Thr Val Trp Ala Gly Asp Val Ala Glu Glu Pro Glu Glu Glu
            500                 505                 510

Asp Asp Gln Leu Gly Asn Leu Asp Glu Glu Ile Lys Lys Met Gln
        515                 520                 525

Ser Asp Glu Gly Thr Ala Gly Leu Glu Val Thr Ala Tyr Glu Glu Met
    530                 535                 540

Ser Ser Leu Val Asn Tyr Ile Gln Pro Ile Lys Phe Asp Ser Phe Glu
545                 550                 555                 560
```

```
Val Ser Ala Gln Lys Asn Arg Ser Tyr Val Ile Ser Ser Phe Thr Glu
                565                 570                 575
Leu Lys Ala Tyr Asp Leu Leu Thr Lys Phe Pro Met Gln Phe Val Glu
            580                 585                 590
Tyr Asn Lys Arg Gln Met Ser Arg Ile Tyr Pro Lys Gly Thr Arg Met
        595                 600                 605
Asp Ser Ser Asn Tyr Met Pro Gln Met Phe Trp Asn Val Gly Cys Gln
    610                 615                 620
Met Val Ala Leu Asn Phe Gln Thr Met Asp Val Pro Met Gln Gln Asn
625                 630                 635                 640
Met Ala Leu Phe Glu Phe Asn Gly Gln Cys Gly Tyr Leu Leu Lys His
                645                 650                 655
Glu Phe Met Arg Arg Pro Asp Lys Gln Phe Asp Pro Phe Ser Val Asp
            660                 665                 670
Arg Ile Asp Val Val Ala Ser Thr Val Ser Val Thr Ile Leu Ser
        675                 680                 685
Gly Gln Phe Leu Ser Asp Arg Ser Val Lys Thr Tyr Val Glu Val Glu
    690                 695                 700
Leu Phe Gly Leu Pro Arg Asp Thr Lys Arg Lys Tyr Arg Thr Lys Leu
705                 710                 715                 720
Thr Ser Thr Ala Asn Ser Ile Asn Pro Val Trp Lys Glu Pro Phe
                725                 730                 735
Val Phe Glu Lys Ile Val Met Pro Glu Leu Ala Ser Leu Lys Ile Val
            740                 745                 750
Ala Phe Glu Glu Gly Gly Lys Phe Ile Gly His Arg Val Ile Pro Ile
        755                 760                 765
Ile Ala Val His Ser Gly Tyr His His Val Cys Leu Arg Ser Glu Ser
    770                 775                 780
Asn Met Pro Leu Thr Met Pro Ser Leu Phe Val Tyr Leu Glu Val Lys
785                 790                 795                 800
Asp Tyr Val Pro Asp Ala Trp Ala Asp Leu Thr Ile Ala Leu Ser Asn
                805                 810                 815
Pro Ile Lys Phe Phe Asn Leu Gln Glu Lys Arg Ser Val Asn Leu Lys
            820                 825                 830
Asp Gly Ser Glu Val Glu Arg Pro Asp Met Gln Arg Asn Phe Ser Phe
        835                 840                 845
Pro Glu Asn Asn Gly Ile Pro Glu Ser Thr Arg Ile Phe Ser Thr Pro
    850                 855                 860
Phe Ala Asn Gly Pro Ala Gly Ala Ala Ala Leu Val Lys Asp Gly Asn
865                 870                 875                 880
Met Lys Glu Val Thr Gln Leu Pro Glu Pro Gln Thr Ala Ser Leu Ala
                885                 890                 895
Glu Leu Gln Gln Met Lys Leu Phe Leu Lys Leu Lys Lys Gln Glu
            900                 905                 910
Lys Glu Leu Lys Glu Leu Glu Arg Lys Gly Ser Lys Arg Arg Glu Glu
        915                 920                 925
Leu Leu Gln Lys Tyr Ser Val Leu Phe Leu Glu Pro Val Tyr Pro Arg
    930                 935                 940
Gly Lys Lys Arg Ser Met His Ser Arg Lys Thr Gln Lys Lys Arg Ser
945                 950                 955                 960
Leu Thr Thr Gly Asp Val Gly Thr Cys Met Gln Pro Val Glu Met Ala
                965                 970                 975
Glu Lys Leu Asp Ser Gln Val Val Glu Leu Lys Glu Arg Leu Glu Met
```

```
                    980                985                990
Glu Leu Ile His Leu Gly Glu Glu  Tyr His Asp Gly Ile  Arg Arg Arg
            995                1000              1005

Lys Glu  Gln His Ala Thr Glu  Gln Thr Ala Lys Ile  Thr Glu Leu
    1010              1015                  1020

Ala Arg  Glu Lys Gln Ile Ala  Glu Leu Lys Ala Leu  Lys Glu Ser
    1025              1030                  1035

Ser Glu  Ser Asn Ile Lys Asp  Ile Lys Lys Lys Leu  Glu Ala Lys
    1040              1045                  1050

Arg Leu  Asp Arg Ile Gln Val  Met Met Arg Ser Thr  Ser Asp Lys
    1055              1060                  1065

Ala Ala  Gln Glu Arg Leu Lys  Lys Glu Ile Asn Asn  Ser His Ile
    1070              1075                  1080

Gln Glu  Val Val Gln Thr Ile  Lys Leu Leu Thr Glu  Lys Thr Ala
    1085              1090                  1095

Arg Tyr  Gln Gln Lys Leu Glu  Glu Lys Gln Ala Glu  Asn Leu Arg
    1100              1105                  1110

Ala Ile  Gln Glu Lys Glu Gly  Gln Leu Gln Gln Glu  Ala Val Ala
    1115              1120                  1125

Glu Tyr  Glu Glu Lys Leu Lys  Thr Leu Thr Val Glu  Val Gln Glu
    1130              1135                  1140

Met Val  Lys Asn Tyr Met Lys  Glu Val Phe Pro Asp  Gly Pro Glu
    1145              1150                  1155

Ile Gln  Lys Glu Ala Val Leu  Ser Ile Pro Val Glu  Glu Gln Gly
    1160              1165                  1170

Ser Thr  Lys Gln Leu Glu Glu  Lys Ile Pro Gly Ala  Glu Val Pro
    1175              1180                  1185

Arg Leu  Thr Ala Ala Thr Thr  Glu Pro Pro Gly Ala  Glu Thr Asp
    1190              1195                  1200

Ile Asn  Ile Glu Glu Ser Ile  Leu
    1205              1210
```

<210> SEQ ID NO 3
<211> LENGTH: 270
<212> TYPE: PRT
<213> ORGANISM: Thermomyces lanuginosus

<400> SEQUENCE: 3

```
Ala Glu Val Ser Gln Asp Leu Phe Asn Gln Phe Asn Leu Phe Ala Gln
1               5                   10                  15

Tyr Ser Ala Ala Ala Tyr Cys Gly Lys Asn Asn Asp Ala Pro Ala Gly
            20                  25                  30

Thr Asn Ile Thr Cys Thr Gly Asn Ala Cys Pro Glu Val Glu Lys Ala
        35                  40                  45

Asp Ala Thr Phe Leu Tyr Ser Phe Glu Asp Ser Gly Val Gly Asp Val
    50                  55                  60

Thr Gly Phe Leu Ala Leu Asp Asn Thr Asn Lys Leu Ile Val Leu Ser
65                  70                  75                  80

Phe Arg Gly Ser Arg Ser Ile Glu Asn Trp Ile Gly Asn Leu Asn Phe
                85                  90                  95

Asp Leu Lys Glu Ile Asn Asp Ile Cys Ser Gly Cys Arg Gly His Asp
            100                 105                 110

Gly Phe Thr Ser Ser Trp Arg Ser Val Ala Asp Thr Leu Arg Gln Lys
        115                 120                 125
```

```
Val Glu Asp Ala Val Arg Glu His Pro Asp Tyr Arg Val Val Phe Thr
    130                 135                 140

Gly His Ser Leu Gly Gly Ala Leu Ala Thr Val Ala Gly Ala Asp Leu
145                 150                 155                 160

Arg Gly Asn Gly Tyr Asp Ile Asp Val Phe Ser Tyr Gly Ala Pro Arg
                165                 170                 175

Val Gly Asn Arg Ala Phe Ala Glu Phe Leu Thr Val Gln Thr Gly Gly
                180                 185                 190

Thr Leu Tyr Arg Ile Thr His Thr Asn Asp Ile Val Pro Arg Leu Pro
                195                 200                 205

Pro Arg Glu Phe Gly Tyr Ser His Ser Ser Pro Glu Tyr Trp Ile Lys
    210                 215                 220

Ser Gly Thr Leu Val Pro Val Thr Arg Asn Asp Ile Val Lys Ile Glu
225                 230                 235                 240

Gly Ile Asp Ala Thr Gly Gly Asn Asn Gln Pro Asn Ile Pro Asp Ile
                245                 250                 255

Pro Ala His Leu Trp Tyr Phe Gly Leu Ile Gly Thr Cys Leu
                260                 265                 270

<210> SEQ ID NO 4
<211> LENGTH: 342
<212> TYPE: PRT
<213> ORGANISM: Candida antarctica

<400> SEQUENCE: 4

Met Lys Leu Leu Ser Leu Thr Gly Val Ala Gly Val Leu Ala Thr Cys
1               5                   10                  15

Val Ala Ala Thr Pro Leu Val Lys Arg Leu Pro Ser Gly Ser Asp Pro
                20                  25                  30

Ala Phe Ser Gln Pro Lys Ser Val Leu Asp Ala Gly Leu Thr Cys Gln
            35                  40                  45

Gly Ala Ser Pro Ser Ser Val Ser Lys Pro Ile Leu Leu Val Pro Gly
        50                  55                  60

Thr Gly Thr Thr Gly Pro Gln Ser Phe Asp Ser Asn Trp Ile Pro Leu
65                  70                  75                  80

Ser Thr Gln Leu Gly Tyr Thr Pro Cys Trp Ile Ser Pro Pro Pro Phe
                85                  90                  95

Met Leu Asn Asp Thr Gln Val Asn Thr Glu Tyr Met Val Asn Ala Ile
                100                 105                 110

Thr Ala Leu Tyr Ala Gly Ser Gly Asn Asn Lys Leu Pro Val Leu Thr
            115                 120                 125

Trp Ser Gln Gly Gly Leu Val Ala Gln Trp Gly Leu Thr Phe Phe Pro
        130                 135                 140

Ser Ile Arg Ser Lys Val Asp Arg Leu Met Ala Phe Ala Pro Asp Tyr
145                 150                 155                 160

Lys Gly Thr Val Leu Ala Gly Pro Leu Asp Ala Leu Ala Val Ser Ala
                165                 170                 175

Pro Ser Val Trp Gln Gln Thr Thr Gly Ser Ala Leu Thr Thr Ala Leu
                180                 185                 190

Arg Asn Ala Gly Gly Leu Thr Gln Ile Val Pro Thr Thr Asn Leu Tyr
            195                 200                 205

Ser Ala Thr Asp Glu Ile Val Gln Pro Gln Val Ser Asn Ser Pro Leu
        210                 215                 220

Asp Ser Ser Tyr Leu Phe Asn Gly Lys Asn Val Gln Ala Gln Ala Val
225                 230                 235                 240
```

```
Cys Gly Pro Leu Phe Val Ile Asp His Ala Gly Ser Leu Thr Ser Gln
            245                 250                 255

Phe Ser Tyr Val Val Gly Arg Ser Ala Leu Arg Ser Thr Thr Gly Gln
            260                 265                 270

Ala Arg Ser Ala Asp Tyr Gly Ile Thr Asp Cys Asn Pro Leu Pro Ala
            275                 280                 285

Asn Asp Leu Thr Pro Glu Gln Lys Val Ala Ala Ala Leu Leu Ala
            290                 295                 300

Pro Ala Ala Ala Ile Val Ala Gly Pro Lys Gln Asn Cys Glu Pro
305                 310                 315                 320

Asp Leu Met Pro Tyr Ala Arg Pro Phe Ala Val Gly Lys Arg Thr Cys
            325                 330                 335

Ser Gly Ile Val Thr Pro
            340
```